(12) United States Patent
Sato et al.

(10) Patent No.: US 7,869,061 B2
(45) Date of Patent: Jan. 11, 2011

(54) SURFACE-DISTORTION MEASURING DEVICE AND METHOD

(75) Inventors: Kentaro Sato, Fukuyama (JP); Takanobu Saito, Chiba (JP); Takashi Iwama, Fukuyama (JP); Akihide Yoshitake, Chiba (JP); Mitsuaki Uesugi, Kawasaki (JP)

(73) Assignees: JFE Steel Corporation, Tokyo (JP); JFE Techno-Research Corporation, Tokyo (JP)

( * ) Notice: Subject to any disclaimer, the term of this patent is extended or adjusted under 35 U.S.C. 154(b) by 438 days.

(21) Appl. No.: 11/991,788

(22) PCT Filed: Sep. 14, 2006

(86) PCT No.: PCT/JP2006/318671

§ 371 (c)(1),
(2), (4) Date: Mar. 11, 2008

(87) PCT Pub. No.: WO2007/034848

PCT Pub. Date: Mar. 29, 2007

(65) Prior Publication Data

US 2009/0141287 A1 Jun. 4, 2009

(30) Foreign Application Priority Data

Sep. 15, 2005 (JP) ............................. 2005-268544
Oct. 26, 2005 (JP) ............................. 2005-311151
Jul. 14, 2006 (JP) ............................. 2006-194514

(51) Int. Cl.
*G01B 11/24* (2006.01)

(52) U.S. Cl. ...................................... 356/610; 356/603

(58) Field of Classification Search ......... 356/600–612, 356/237.2, 239.7, 239.1, 32, 445; 250/341.8, 250/345, 339.06, 339.11, 572, 559.11, 574; 348/128
See application file for complete search history.

(56) References Cited

U.S. PATENT DOCUMENTS

| 4,647,197 A * | 3/1987 | Kitaya et al. ............. 356/239.1 |
| 5,309,222 A * | 5/1994 | Kamei et al. ............. 356/613 |
| 6,239,436 B1 * | 5/2001 | Parker et al. ............. 250/341.8 |

FOREIGN PATENT DOCUMENTS

| JP | A-60-119404 | 6/1985 |
| JP | A-1-165907 | 6/1989 |
| JP | A-3-135704 | 6/1991 |
| JP | A-3-199946 | 8/1991 |

(Continued)

*Primary Examiner*—Gregory J Toatley
*Assistant Examiner*—Tri T Ton
(74) *Attorney, Agent, or Firm*—Oliff & Berridge, PLC

(57) ABSTRACT

A surface-distortion measuring device and a surface-distortion measuring method can quantitatively, rapidly, and highly accurately measure and evaluate surface-distortion distribution at all of observable points on a specular or semi-specular surface of a measurement target. The device includes pattern displaying means 2 capable of switching and displaying a plurality of kinds of light-and-shade patterns 5, capturing means 3 for capturing mirror images, reflected in the specular or semi-specular surface of a measurement target 1, of the plurality of light-and-shade patterns displayed on the pattern displaying means, and surface-distortion distribution calculating means 10 for performing image processing on the captured mirror images of the plurality of light-and-shade patterns to calculate surface-distortion distribution of the measurement-target surface.

18 Claims, 19 Drawing Sheets

FOREIGN PATENT DOCUMENTS

| | | |
|---|---|---|
| JP | A-7-20059 | 1/1995 |
| JP | A-8-220021 | 8/1996 |
| JP | A-11-153420 | 6/1999 |
| JP | A-2002-22665 | 1/2002 |
| JP | A-2002-257528 | 9/2002 |
| JP | A-2003-279332 | 10/2003 |
| JP | A-2004-251878 | 9/2004 |
| JP | A-2005-3409 | 1/2005 |

* cited by examiner

FIG. 5A
FIG. 5B
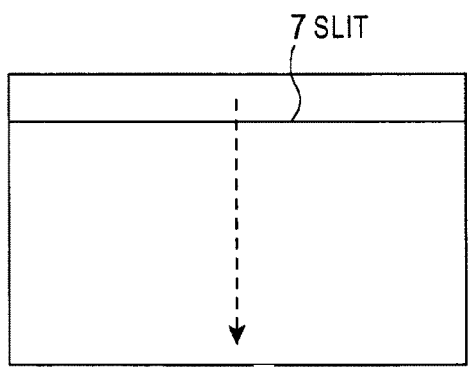
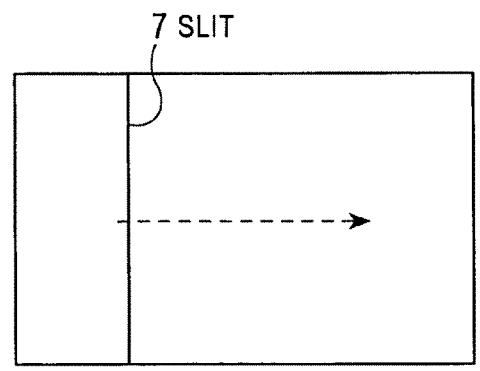

SURFACE-DISTORTION MEASURING DEVICE AND METHOD

TECHNICAL FIELD

The present invention relates to surface-distortion measuring devices and surface-distortion measuring methods. More specifically, the present invention relates to surface-distortion measuring devices and surface-distortion measuring methods for quantitatively measuring and evaluating surface-distortion distribution at all observable points on a specular or semi-specular surface of a measurement target using optical means.

BACKGROUND ART

If a wavy distortion, so-called "surface distortion", exists on a surface of industrial products having specular or semi-specular surfaces, such as press-formed and coated vehicle outer panels, coated architectural wall panels, or flat glass mirrors, a reflected background image looks significantly distorted due to the principle of "optical lever" no matter how small the distortion is. This considerably defaces the appearance of the industrial products and inflicts great damage on the quality thereof.

The above-described distortion is caused at any steps of performing a series of processing operations, such as press-forming, assembling, and coating of a metal plate. During the press-forming, a surface of a press-formed product may deform due to the elastic deformation after the mold-releasing, and a distortion is possibly caused. Additionally, when an extraneous matter, such as iron powder, attaches to a press die, a distortion may be caused on the press-formed product. In addition, when a crack or a wrinkle is caused on a part of the press-formed product in the course of the press-forming, the tension of the product changes, which induces a distortion. During the assembling, caulking or welding may cause a distortion. During the coating, thermal deflection and coating unevenness due to baking, and attachment of an extraneous matter may cause a distortion.

Accordingly, a technique for quantitatively measuring surface-distortion distribution has been desired at sites of product development and manufacturing, such as evaluation, building of the quality, and quality inspection of materials of these industrial products.

However, it is extremely difficult to perform a quantitative shape measurement all over a surface of a target to measure the ruggedness of approximately 10 μm to 100 μm on the surface of the target of several hundreds millimeters to several meters in size. Hitherto, a method for determining distribution of small shape distortions by performing x-y scanning on a surface of a target using a non-contact rangefinder represented by a laser displacement gauge has been known. However, the method takes a lot of time to perform the measurement, and is not a practical method.

On the other hand, hitherto, a method for evaluating a surface distortion on the basis of the degree of deformation utilizing a phenomenon that an mirror image of a background stripe pattern or a background checker board pattern reflected in a surface of a target looks distorted due to the surface distortion has been known as a method for performing quantitative pattern observation of a surface distortion.

A method disclosed in Patent Document 1 is one of qualitative surface-distortion observation methods that mainly target at mirror-coated large architectural panels. The method attempts to determine the degree of surface distortion on the basis of a magnitude relation between a line-width and a line-interval of a predetermined line included in several kinds of stripe patterns having different line-widths and line-intervals reflected in the panel and thresholds therefor.

In addition, a method disclosed in Patent Document 2, Patent Document 3, Patent Document 4, or Patent Document 5 has been suggested mainly as a method for observing a distortion on and inside a glass. The method attempts to evaluate the distortion on the basis of a degree of deformation, a curvature, a line-width, and a line-interval of a reflected image reflected on a surface of the measurement-target glass or a transmitted image inside the glass by observing the reflected image or the transmitted image of a stripe pattern or a checker board pattern.

On the other hand, Patent Document 6, Patent Document 7, or Patent Document 8 advances the above-described observation methods by one step, and discloses an attempt to quantify this distortion. These methods attempt to quantify the distortion by focusing on a fact that a contrast or a phase shift of a stripe pattern or a checker board pattern, or a generated moiré fringe changes depending on the degree of distortion.

In addition, Patent Document 9 discloses a method for sensitively detecting a small rugged defect on a semi-specular coated surface of a body of a vehicle, although the object of the method is more or less different from the surface-distortion measurement. In this method, a slit diffusion illumination light is irradiated, and a timing at which a mirror image of the slit reflected in the surface of the measurement target passes each point on the surface of the target is determined by image synthesis. The method attempts to detect a defect on the basis of a partial distortion of a timing pattern resulting from the small rugged defect. This method can be transferred to observation of surface distortions, and provides a robust observation method for shapes of a target.

Patent Document 10 discloses a method for determining fine ruggedness distribution. In the method, a plurality of kinds of stripe array patterns used in the binary-coded pattern projection method are sequentially projected from a point-source light. The projected patterns are photographed, and the photographed images are processed to determine coarse ruggedness distribution. Processing for scanning slits, parallel to the one pair of the stripes, in a direction orthogonal to a stripe-extending direction in a range covered with one pair of light and shade stripes in one stripe array pattern from the stripe array patterns is simultaneously performed on all pairs of stripes. During the scanning of slits, coordinate values of positions of the slit-scanning at the time that each pixel shows the maximum brightness are captured all over the image. Ultimately, the coarse ruggedness distribution determined by sequentially displaying the above-described stripe array patterns is complemented by the fine ruggedness distribution determined by scanning the slits, thereby determining the overall fine ruggedness distribution.

Here, the binary-coded pattern projection method is a position recognition method for sequentially projecting a plurality of kinds of stripe array patterns, temporarily recognizing a position as a corresponding binary number on the basis of a pattern whose light and shade are switched according to the position, and ultimately recognizing the position as a decimal number after converting the binary number into the decimal number as shown in FIG. 15. The stripe array pattern may be, for example, a stripe array pattern having light and shade alternately arranged at $2^n$ equally divided sections.

For example, FIG. 15 shows a state in which first to third-order patterns are sequentially projected onto a reference surface 20 from a point-source light 15. A light-and-shade pattern displayed on a leftmost section corresponding to "7", among positions represented by decimal numbers corresponding to n-th positions from the left of sections shown in the bottom, is recognized as a corresponding binary number, such as "1" for light in the first-order pattern, "1" for light in the second-order pattern, and "1" for light in the third-order patter, thus the position is recognized as $2^2 \times 1 + 2^{2-1} \times 1 + 2^{2-2} \times 1 = 7$. Similarly, a light-and-shade pattern displayed on the second section from the left corresponding to "6" among the positions represented by decimal numbers corresponding to the sections shown in the bottom is recognized as a corresponding binary number, such as "1" for light in the first-order pattern, "1" for light in the second-order pattern, and "0" for shade in the third-order pattern, thus the position is recognized as $2^2 \times 1 + 2^{2-1} \times 1 + 2^{2-2} \times 0 = 6$. Likewise, a light-and-shade pattern displayed on the third section from the left corresponding to "5" among the positions represented by decimal numbers corresponding to the sections shown in the bottom is recognized as a corresponding binary number, such as "1" for light in the first-order pattern, "0" for shade in the second-order pattern, and "1" for light in the third-order pattern, thus the position is recognized as $2^2 \times 1 + 2^{2-1} \times 0 + 2^{2-2} \times 1 = 5$. That is how the position is recognized.

The cited Patent Documents are collectively listed below.

Patent Document 1: Japanese Unexamined Patent Application Publication No. 11-153420

Patent Document 2: Japanese Unexamined Patent Application Publication No. 60-119404

Patent Document 3: Japanese Unexamined Patent Application Publication No. 1-165907

Patent Document 4: Japanese Unexamined Patent Application Publication No. 3-135704

Patent Document 5: Japanese Unexamined Patent Application Publication No. 3-199946

Patent Document 6: Japanese Unexamined Patent Application Publication No. 7-20059

Patent Document 7: Japanese Unexamined Patent Application Publication No. 8-220021

Patent Document 8: Japanese Unexamined Patent Application Publication No. 2004-251878

Patent Document 9: Japanese Unexamined Patent Application Publication No. 2002-22665

Patent Document 10: Japanese Unexamined Patent Application Publication No. 2005-3409

However, techniques disclosed in Patent Documents 2 to 5 only visualize the distortion, and does not guarantee quantification of measured values.

In addition, in techniques disclosed in Patent Documents 6 to 8, the measurement result is likely to be affected by the light-and-shade of the projected stripe pattern or checker board pattern. Additionally, an observable area is limited to an area near the edge of the light-and-shade portion of the pattern or a spatial resolution is limited due to averaging. Accordingly, the limitation is imposed on the efficiency.

Furthermore, in a technique disclosed in Patent Document 9, a problem remains in that a time required for measurement is long since a mirror image is scanned with one slit and in that quantitative evaluation equation between the timing lags and the degree of surface distortion is not established.

Moreover, in a technique disclosed in Patent Document 10, values of coordinates in the slit-scanning direction at the time that each pixel shows the maximum brightness are determined by measuring an angle θ shown in FIG. 15. Thus, as a matter of limitation on resolution of the angle θ, it is possible to easily perform quantitative measurement of ruggedness of approximately several millimeters, such as, for example, ups and downs of a person's face. However, it is impossible to perform quantitative measurement of surface-distortion distribution equivalent to small ruggedness of approximately several tens micrometers on a specular surface or semi-specular surface, such as, for example, a surface of a vehicle outer panel.

In addition, when inspection of surface quality-defects resulting from a surface distortion is performed in each of metal-plate processing steps of performing at least one of press-forming, component mounting, assembling, coating, heat treatment, and inspection of a finished product, it is necessary to inspect the product moving on the manufacturing line at a high-speed. However, conventional techniques cannot cope with the speed of product moving on the manufacturing line, and it is impossible to perform inline inspection.

In view of these problems in the related art, it is an object of the present invention to provide surface-distortion measuring device and method capable of quantitatively, rapidly, and highly accurately measuring and evaluating surface-distortion distribution at all of observable points on a specular or semi-specular surface of a measurement target.

DISCLOSURE OF INVENTION

A first invention of the present invention is a device for measuring a surface distortion on a specular surface or a semi-specular surface characterized by including: pattern displaying means capable of switching and displaying a plurality of kinds of light-and-shade patterns; capturing means for capturing mirror images, reflected in the specular or semi-specular measurement-target surface, of the plurality of light-and-shade patterns displayed on the pattern displaying means; and surface-distortion distribution calculating means for performing image processing on the captured mirror images of the plurality of light-and-shade patterns to calculate surface-distortion distribution of the measurement-target surface.

A second invention of the present invention is the device for measuring a surface distortion on a specular surface or a semi-specular surface according to the first invention, characterized by comprising: pattern displaying means capable of displaying the mirror images captured by the capturing means as images.

A third invention of the present invention is the device for measuring a surface distortion on a specular surface or a semi-specular surface according to the first or second invention, characterized by comprising: measurement-calculation-result displaying means capable of displaying a processing result of an intermediate stage or a final stage of the image processing and/or a surface-distortion calculation result.

A fourth invention of the present invention is the device for measuring a surface distortion on a specular surface or a semi-specular surface according to any one of the first to third inventions, characterized in that the pattern displaying means is capable of displaying the light-and-shade patterns using a plurality of kinds of stripe array patterns used for a binary-coded pattern projection method and a plurality of slits, each of which scans a range equal to or greater than a minimum stripe width.

A fifth invention of the present invention is the device for measuring a surface distortion on a specular surface or a semi-specular surface according to the fourth invention, characterized in that the plurality of kinds of stripe array patterns are patterns in which the whole area of a stripe array pattern is equally divided into $2^n$ pieces and light and shade are alternately arranged.

A sixth invention of the present invention is the device for measuring a surface distortion on a specular surface or a semi-specular surface according to the fourth or fifth invention, characterized in that the plurality of slits are scanned in a direction orthogonal to a direction in which the slits extend.

A seventh invention of the present invention is the device for measuring a surface distortion on a specular surface or a semi-specular surface according to any one of the fourth to sixth inventions, characterized in that a plurality of kinds of second stripe array patterns and a plurality of second slits, whose extending directions are orthogonal to those of the plurality of kinds of stripe array patterns and the plurality of slits, are used instead of the plurality of kinds of stripe array patterns and the plurality of slits.

An eighth invention of the present invention is the device for measuring a surface distortion on a specular surface or a semi-specular surface according to any one of the first to seventh inventions, characterized in that the pattern displaying means is constituted by a projector capable of projecting given patterns and a screen.

A ninth invention of the present invention is the device for measuring a surface distortion on a specular surface or a semi-specular surface according to any one of the first to seventh inventions, characterized in that the pattern displaying means is constituted by a flat-panel display capable of displaying given patterns.

A tenth invention of the present invention is the device for measuring a surface distortion on a specular surface or a semi-specular surface according to any one of the fourth to ninth inventions, the surface-distortion measuring device calculating the surface-distortion distribution on the basis of mirror images of the plurality of kinds of stripe array patterns used for the binary-coded pattern projection method, the device characterized by storing, for each pixel of the capturing means, an order of appearance of light and shade at the pixel during switching and displaying of the plurality of kinds of stripe array patterns, by determining a value of coordinates, on the pattern displaying means, corresponding to the stored result of the appearance order, by determining a value of coordinates, on the measurement-target surface, corresponding to the pixel on the basis of the determined coordinate value, an address of the pixel, and a geometric relationship between the pattern displaying means, the capturing means, and the measurement target, and by determining coarse surface-distortion distribution of the whole measurement-target surface on the basis of the coordinate value on the pattern display means corresponding to the pixel and the coordinate value on the measurement-target surface corresponding to the pixel.

An eleventh invention of the present invention is the device for measuring a surface distortion on a specular surface or a semi-specular surface according to the tenth invention, the surface-distortion measuring device calculating surface-distortion distribution on the basis of the plurality of mirror images obtained by scanning the plurality of slits, the device characterized by determining, for each pixel, a value of coordinates of a position of the slit-scanning on the pattern displaying means at the time that the corresponding pixel of the capturing means shows the maximum brightness during the scanning of the slits as a value of coordinates on the pattern displaying means corresponding to the pixel, by determining fine surface-distortion distribution within a range equal to or greater than the minimum stripe width on the basis of the determined coordinate value, an address of the corresponding pixel, and a geometric relationship between the pattern displaying means, the capturing means, and the measurement target, and by displaying an image of the fine surface-distortion distribution.

A twelfth invention of the present invention is the device for measuring a surface distortion on a specular surface or a semi-specular surface according to the eleventh invention, characterized in that the calculation result of the coarse surface-distortion distribution of the whole measurement-target surface determined on the basis of the mirror images of the plurality of kinds of stripe array patterns used for the binary-coded pattern projection method is complemented by the fine surface-distortion distribution within the range equal to or greater than the minimum stripe width determined on the basis of the plurality of mirror images obtained by scanning the plurality of slits to determine fine surface-distortion distribution of the whole measurement-target surface.

A thirteenth invention of the present invention is the device for measuring a surface distortion on a specular surface or a semi-specular surface according to any one of the fourth to ninth inventions, characterized in that the image processing or the surface-distortion distribution calculation performed by the surface-distortion distribution calculating means includes a step of storing, for each pixel of the capturing means, an order of appearance of light and shade at the pixel during switching and displaying of the plurality of kinds of stripe array patterns and of determining a value of coordinates, on the pattern displaying means, corresponding to the stored result of the appearance order as a value of coordinates on the pattern display means corresponding to the pixel, a step of determining, for each pixel, a value of coordinates of a position of the slit-scanning on the pattern displaying means at the time that the corresponding pixel of the capturing means shows the maximum brightness during the scanning of the slits as a value of coordinates on the pattern displaying means corresponding to the pixel, a step of combining the coordinate values to determine a value of coordinates on the pattern displaying means corresponding to each pixel, a step of determining, for all of pixels, surface-distortion distribution on the basis of the determined coordinate value, an address of each pixel, and a geometric relationship between the pattern displaying means, the capturing means, and the measurement target, and a step of displaying an image of an execution result obtained at one or more steps among the above-described steps.

A fourteenth invention of the present invention is the device for measuring a surface distortion on a specular surface or a semi-specular surface according to any one of the first to thirteenth inventions, characterized in that the rate of change in inclination of the surface is calculated by determining a second derivative of the inclination of the measurement-target surface and a position of the surface distortion and the degree of the surface distortion are evaluated quantitatively.

A fifteenth invention of the present invention is a method for measuring a surface distortion on a specular surface or a semi-specular surface, characterized by performing: processing for displaying a plurality of kinds of stripe array patterns used for a binary-coded pattern projection method on pattern displaying means capable of displaying given patterns; processing for scanning and displaying a plurality of slits in a direction orthogonal to a direction in which the slits extend; processing for capturing mirror images, reflected in the specular or semi-specular measurement-target surface, of the plurality of displayed stripe array patterns with capturing means; processing for storing, for each pixel of the capturing means for capturing the mirror images, of the plurality of stripe array patterns used for the binary-coded pattern projection method, reflected in the measurement target, an order of appearance of light and shade at the pixel, for determining a value of coordinates, on the pattern displaying means, corresponding to the stored result of the order of appearance as a value of coordinates on the pattern displaying means corresponding to the pixel, for determining a value of coordinates on the measurement-target surface corresponding to the pixel on the basis of the determined coordinate value, an address of the pixel, and a geometric relationship between the pattern displaying means, the capturing means, and the measurement target, and for determining coarse surface-distortion distribution of the whole measurement-target surface on the basis of the coordinate value on the pattern display means corresponding to the pixel and the coordinate value on the measurement-target surface corresponding to the pixel; processing for determining, for each pixel, a value of coordinates of a position of the slit-scanning on the pattern displaying means at the time that the pixel shows the maximum brightness during the scanning of the slits as a value of coordinates on the pattern displaying means corresponding to the pixel and displaying an image of the data, and for determining, for all of the pixels, fine surface-distortion distribution within a range equal to or greater than the minimum stripe width on the basis of the determined coordinate value, an address of the pixel, and a geometric relationship between the pattern displaying means, the capturing means, and the measurement target; and processing for determining fine surface-distortion distribution of the whole measurement-target surface by complementing the calculation result of the overall coarse surface-distortion distribution with the calculation result of the fine surface-distortion distribution.

A sixteenth invention of the present invention is a method for measuring a surface distortion on a specular surface or a semi-specular surface, characterized by performing: processing for displaying a plurality of kinds of stripe array patterns used for a binary-coded pattern projection method on pattern displaying means capable of displaying given patterns; processing for scanning and displaying a plurality of slits in a direction orthogonal to a direction in which the slits extend; processing for capturing mirror images, reflected in the specular or semi-specular measurement-target surface, of the plurality of displayed stripe array patterns with capturing means; processing for storing, for each pixel of the capturing means for capturing the mirror images, of the plurality of kinds of stripe array patterns used for the binary-coded pattern projection method, reflected in the measurement target, an order of appearance of light and shade at the pixel, for determining a value of coordinates, on the pattern displaying means, corresponding to the stored result of the order of appearance as a value of coordinates on the pattern displaying means corresponding to the pixel; processing for determining, for each pixel, a value of coordinates of a position of the slit-scanning at the time that the pixel shows the maximum brightness during the scanning of the slits as a value of coordinates on the pattern displaying means corresponding to the pixel; processing for combining the coordinate values to determine a value of coordinates on the pattern displaying means corresponding to each pixel; processing for determining, for all of pixels, surface-distortion distribution of the whole measurement-target surface on the basis of the determined coordinate value, an address of the pixel, and a geometric relationship between the pattern displaying means, the capturing means, and the measurement target; and processing for displaying an image of an execution result of an intermediate stage or a final stage of each processing.

A seventeenth invention of the present invention is the method for measuring a surface distortion on a specular surface or a semi-specular surface according to the fifteenth or sixteenth invention, characterized in that the rate of change in inclination of the surface is calculated by determining a second derivative of the inclination of the measurement-target surface and a position of the surface distortion and the degree of the surface distortion are evaluated quantitatively.

An eighteenth invention of the present invention is a method for press-forming a metal plate, characterized in that surface-distortion distribution of the press-formed metal plate is measured using the device for measuring a surface distortion on a specular surface or a semi-specular surface according to any one of the first to fourteenth inventions and/or the method for measuring a surface distortion on a specular surface or a semi-specular surface according to any one of the fifteenth to seventeenth inventions.

A nineteenth invention of the present invention is a method for inspecting quality of a surface of a metal product, characterized in that a surface quality defect resulting from a surface distortion caused in at least one of metal plate processing steps of press-forming, component mounting, assembling, coating, heat treatment, and inspection of a finished product is inspected using the device for measuring a surface distortion on a specular surface or a semi-specular surface according to any one of the first to fourteenth inventions and/or the method for measuring a surface distortion on a specular surface or a semi-specular surface according to any one of the fifteenth to seventeenth inventions.

BRIEF DESCRIPTION OF THE DRAWINGS

FIG. 5A and FIG. 5B are diagrams for describing slit scanning that is one kind of light-and-shade pattern.

REFERENCE NUMERALS

Figure 1:
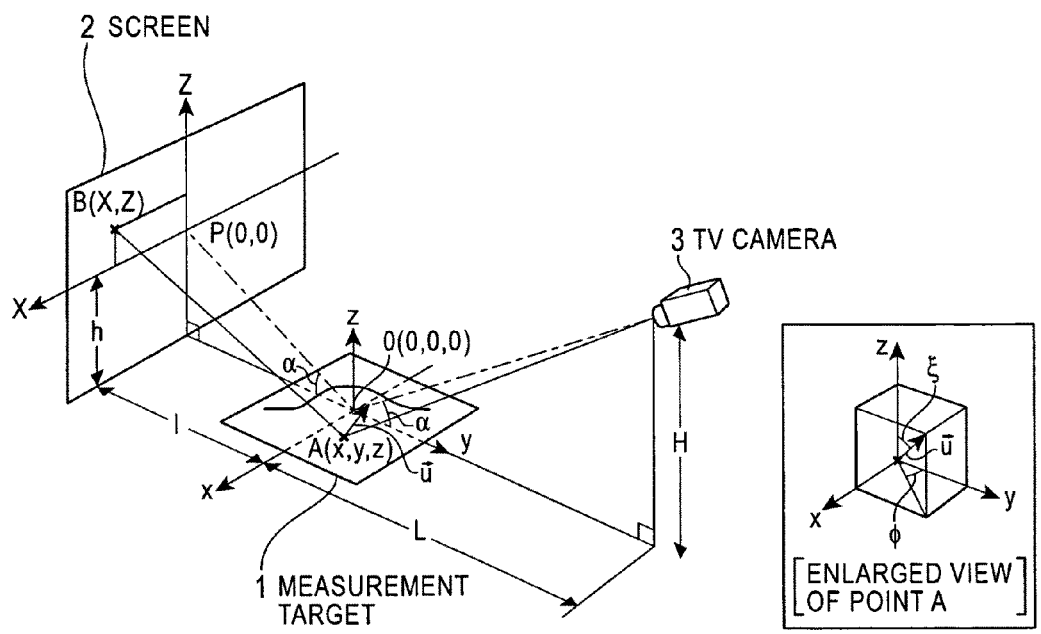
FIG. 1 is a diagram for describing a measurement principle of the present invention.

Reference numerals in the drawings are as follows.

1 represents a measurement target, 2 represents a screen (pattern displaying means; used together with a projector), 3 represents a TV camera (capturing means), 4 represents a flat-panel display (pattern displaying means), 5 represents a stripe array pattern (light-and-shade pattern), 6 represents a projector (pattern displaying means; used together with a screen), 7 represents a slit (light portion of light-and-shade pattern), 10 represents a personal computer, 15 represents a point-source light, 20 represents a reference surface, 101 represents a sequence controlling unit, 102 represents a surface-distortion calculating unit (surface-distortion distribution calculating means), 103 represents a image buffer, and 104 represents a pattern projecting unit.

BEST MODE FOR CARRYING OUT THE INVENTION

The present invention utilizes a phenomenon that a light-and-shade pattern reflected in a specular or semi-specular measurement-target surface is distorted due to a surface distortion. Patterns of a plurality of light-and-shade patterns displayed on pattern displaying means (for example, a screen) reflected in a measurement-target surface, namely, mirror images of the plurality of light-and-shade patterns reflected in the measurement-target surface, are captured using capturing means (for example, a television (TV) camera). Image processing is performing on the captured images, and coordinates of a point on the pattern displaying means (a display surface thereof) corresponding to each point on the measurement-target surface are determined. The degree of surface distortion is calculated on the basis of a measurement principle described below. Furthermore, surface-distortion distribution is determined by performing this calculation for every observable point on the measurement-target surface.

FIG. 1 is a diagram for describing a measurement principle of the present invention. Firstly, the measurement principle of the present invention will be described using this drawing.

In the present invention, for example, a screen 2 serving as pattern displaying means capable of displaying light-and-shade patterns is disposed on one side with respect to a specular or semi-specular surface of a measurement target 1. On the other side, for example, a TV camera 3 serving as capturing means is disposed at a position, from which mirror images, of the light-and-shade patterns displayed on the screen 2, reflected in the measurement-target surface can be observed to observe the mirror images.

In FIG. 1, coordinate systems of the measurement target 1 are represented as (x, y, z). The screen 2 stands vertically at a position apart from a reference point 0 on the measurement target 1 by a distance 1 (small letter of L) in the negative y-direction. The TV camera 3 is disposed apart from the reference point 0 by a projection distance L in the positive y-direction. The -x-y plane is assumed as a horizontal plane. An elevation angle of the TV camera 3 looked up from the reference point 0 is set as α. A point on the screen 2 corresponding to the reference point 0 seen by the TV camera 3 is set as P. The coordinate systems on the screen 2 are represented as (X, Z) using the point P as its origin.

At this time, coordinates of a point A on the measurement-target surface is set as (x, y, z). A unit vector U indicating a direction of a surface distortion at the point A (to be precise, a unit vector in the normal direction of the measurement-target surface having the surface distortion, and hereinafter referred to as a surface-distortion unit vector) is set as U(sin ϵ sin φ, sin ϵ cos φ, cos ϵ) using an angle φ relative to the y-axis and an angle ϵ relative to the z-axis as shown in [ENLARGED VIEW OF POINT A] in FIG. 1. In this case, coordinates (X, Z) of a corresponding point B on the screen 2 when the point A is observed by the TV camera 3 can be approximately determined as Equations (1) and (2) on the basis of the geometric relationship.

$$X = (1+M)x + 2l \tan \alpha \sin \phi \tan \xi \quad (1)$$

$$Z = (1-M)z + (1+M)y \tan \alpha + 2l(1+\tan^2 \alpha) \cos \phi \tan \xi \quad (2)$$

where, $M = l/L$ approximation conditions: $\epsilon \ll 1$, $x,y,z \ll l,L$

If coordinates of a point on the screen corresponding to each point on the measurement-target surface can be determined, a slope sin φ tan ϵ of the surface-distortion unit vector in the x-direction (to be precise, a tangent of an angle between the orthogonal projection of the surface-distortion unit vector to the x-z plane and the z-axis) and a slope cos φ tan ϵ in the y-direction (to be precise, a tangent of an angle between the orthogonal projection of the surface-distortion unit vector to the y-z plane and the z-axis) can be determined as Equations (3) and (4) by transforming Equations (1) and (2), respectively.

$$\sin\phi\tan\xi = \frac{X - (1+M)x}{2l\tan\alpha} \quad (3)$$

$$\cos\phi\tan\xi = \frac{Z - (1-M)z - (1+M)y\tan\alpha}{2l(1+\tan^2\alpha)} \quad (4)$$

where, $M = 1/L$ approximation conditions: $\epsilon \ll 1$, $x,y,z \ll l,L$

To calculate Equations (3) and (4), since the right side of Equation (4) includes "z", information on the rugged shape at the point is necessary in addition to coordinates (x, y) of each point on the measurement-target surface. This rugged shape information (value of z) can be determined by the method described in, for example, Patent Document 10.

When an arrangement of M=l/L=1, i.e., the distance (l) between the reference point 0 and the screen=the projection distance (L) between the reference point 0 and the TV camera, is employed in FIG. 1, a coefficient (1-M) of "z" included in the right side of Equation (4) becomes equal to 0, and an effect of the rugged shape of the measurement-target surface is canceled. Accordingly, more simplified Equations (5) and (6) for surface-distortion calculation can be obtained.

When $l = L$ (5)
$$\sin\phi\tan\xi = \frac{X - 2x}{2l\tan\alpha}$$

$$\cos\phi\tan\xi = \frac{Z - 2y\tan\alpha}{2l(1 + \tan^2\alpha)}$$ (6)

approximation conditions: $\epsilon \ll 1$, $x,y,z \ll l,L$

To determine the surface-distortion distribution on the measurement-target surface by actually applying the above-described measurement principle, means for determining coordinates of a point on the screen corresponding to each point on the measurement-target surface capturable by the TV camera is necessary.

This means can be realized by a measuring device (a first invention of the present invention) including pattern displaying means capable of switching and displaying a plurality of kinds of light-and-shade patterns, capturing means for capturing mirror images, reflected in the specular surface or semi-specular measurement-target surface, of the plurality of light-and-shade patterns displayed on the pattern displaying means, and surface-distortion distribution calculating means for performing image processing on the captured mirror images of the plurality of light-and-shade patterns to calculate surface-distortion distribution of the measurement-target surface.

Figure 2:
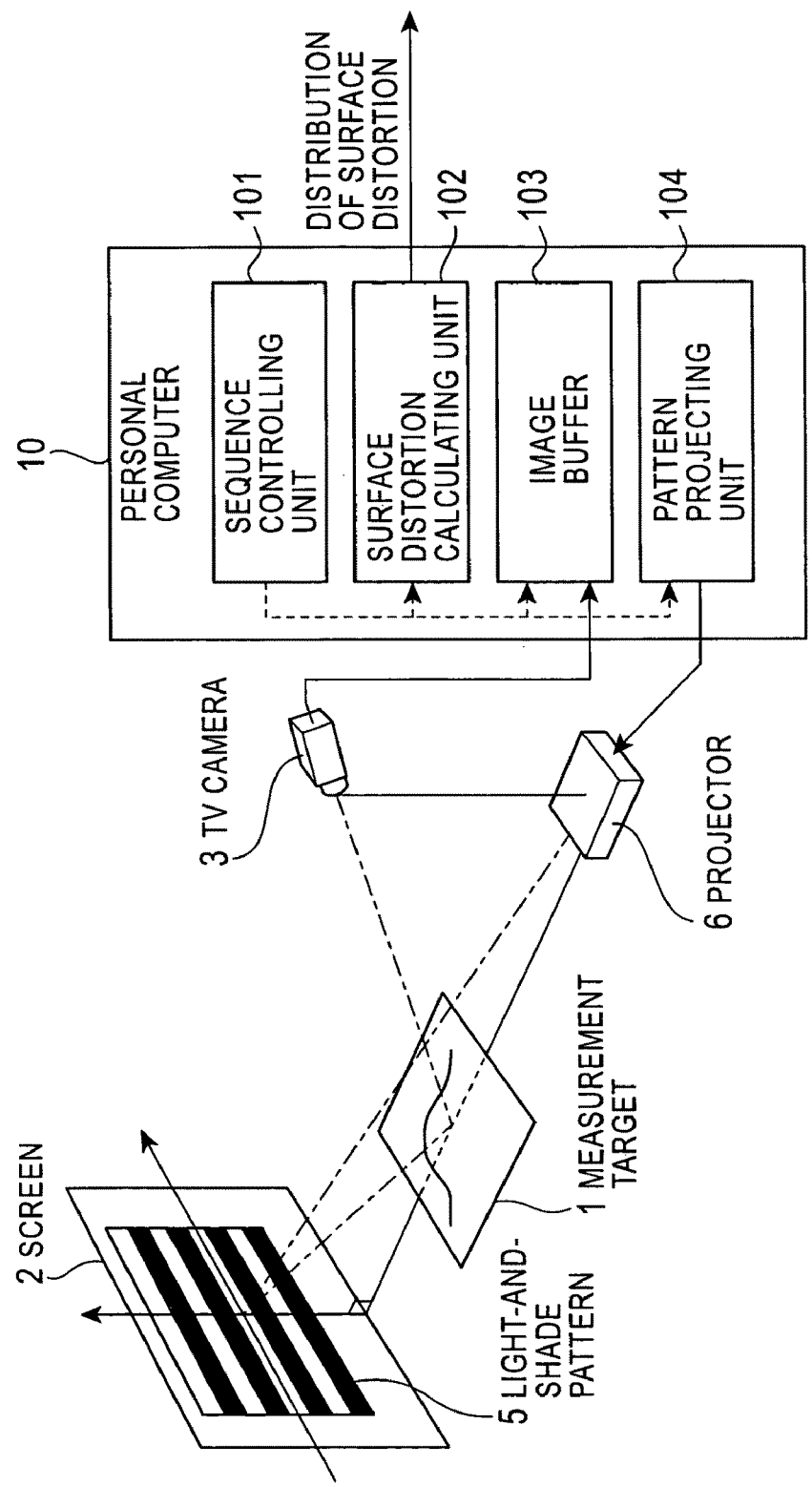
FIG. 2 is a diagram showing an embodiment (a first one) of the present invention.

FIG. 2 is a diagram showing an embodiment (a first one) of the present invention. The pattern displaying means are configured to project light-and-shade patterns 5 onto a screen 2 from a projector 6 (an eighth invention of the present invention). The light-and-shade pattern 5 projected onto the screen 2 is reflected by the specular or semi-specular surface of the measurement target 1 therefrom, whereby a mirror image thereof is reflected in the surface of the measurement target 1. This mirror image is captured by a TV camera 3, serving as the capturing means, disposed at the position from which the mirror image is observable. The projector 6 and the TV camera 3 are connected to a PC (personal computer) 10. The PC 10 includes a pattern projecting unit 104 for sequentially sending a plurality of kinds of light-and-shade patterns to the projector 6, an image buffer 103 for temporarily storing images captured by the TV camera 3, a surface-distortion calculating unit 102 for performing image processing on the captured images temporarily stored in the image buffer 103 to calculate surface-distortion distribution, and a sequence controlling unit 101 for controlling operation sequences or operation timings of the pattern projecting unit 104, the image buffer 103, and the surface-distortion calculating unit 102. According to control operations of the sequence controlling unit 101, the projector 6 can switch, project, and display the plurality of kinds of light-and-shade patterns onto the screen 2. In addition, the surface-distortion calculating unit 102 can operate as surface-distortion distribution calculating means.

Regarding the projector and the TV camera, the former one can be readily realized by devices employing a liquid crystal and DLP (digital light processing), whereas the latter one can be readily realized by devices employing a CCD or the like. The DLP projector performs projection by controlling a reflection angle of DMDs (digital micromirror devices), and is capable of controlling light-and-shade patterns to be projected at a high speed. The number of pixels of these devices can be appropriately selected according to the target measurement accuracy. For example, the number of pixels of 1024×768 may be selected in the projector and the number of pixels of 600×480 may be selected in the TV camera, which is enough for the purpose of the present invention. In addition, from the standpoint of the balance of the accuracy of the both devices, the number of pixels in the vertical and horizontal directions of the projector may be set to approximately once to double of the number of pixels of the TV camera.

Figure 3:
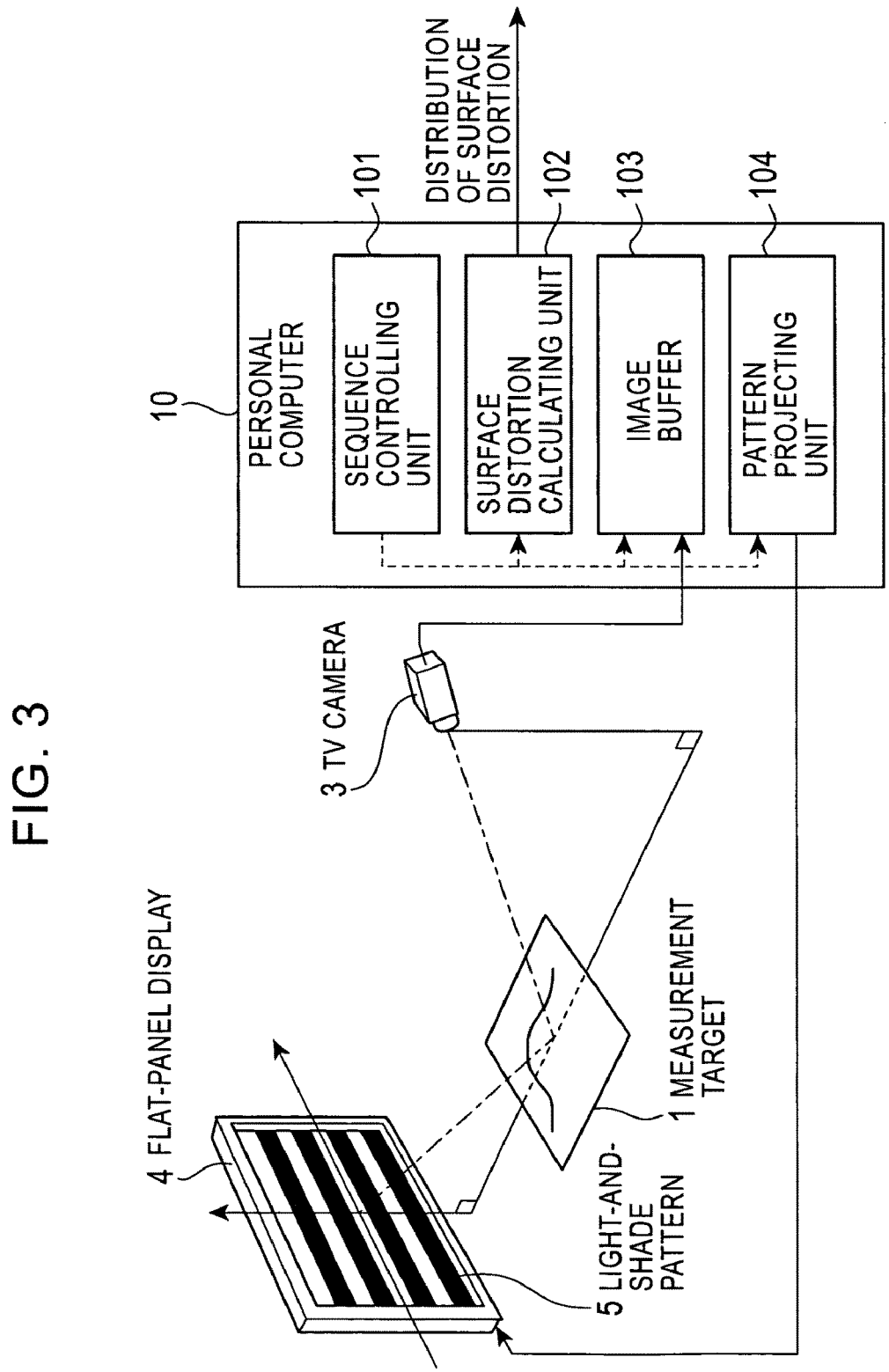
FIG. 3 is a diagram showing an embodiment (a second one) of the present invention.

FIG. 3 is a diagram showing an embodiment (a second one) of the present invention. This corresponds to one in which a flat-panel display 4 is employed as the pattern displaying means instead of the projector 6 and the screen 2 (a ninth invention of the present invention). The flat-panel display 4 may be constituted by a liquid crystal display or a plasma display. The flat-panel display 4 can sequentially display a plurality of kinds of light-and-shade patterns sequentially sent from the pattern projecting unit 104 on a display screen thereof.

A monitor (illustration thereof is omitted) may be connected to the TV camera 3, and can be used as pattern displaying means for displaying captured mirror images as images (corresponding to a second invention of the present invention). In addition, a dedicated display (illustration thereof is omitted) may be connected to the PC 10. The dedicated display can be used as pattern displaying means for displaying the mirror images as images as in the case of the monitor (corresponding to the second invention of the present invention) and can be used as measurement-calculation-result displaying means for displaying a processing result at an intermediate stage or a final stage of image processing and/or a surface-distortion calculation result (corresponding to a third invention of the present invention).

Figure 14:
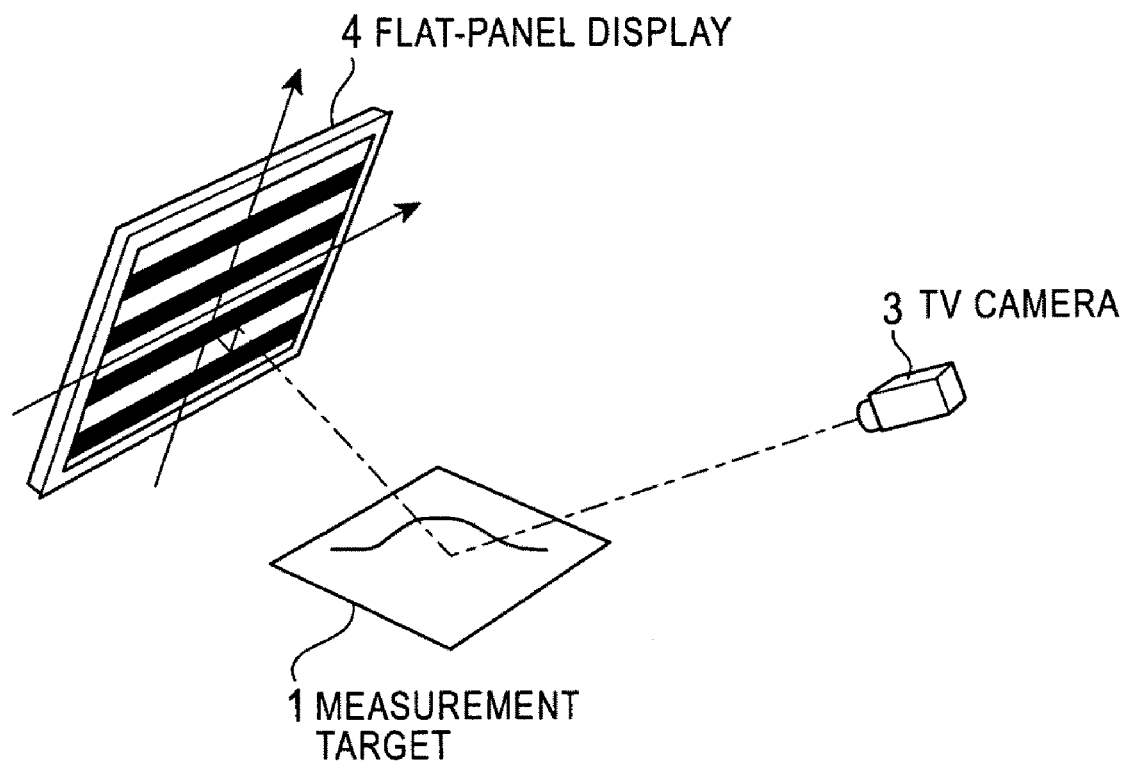
FIG. 14 is a diagram showing an embodiment (a third one) of the present invention.
Figure 15:
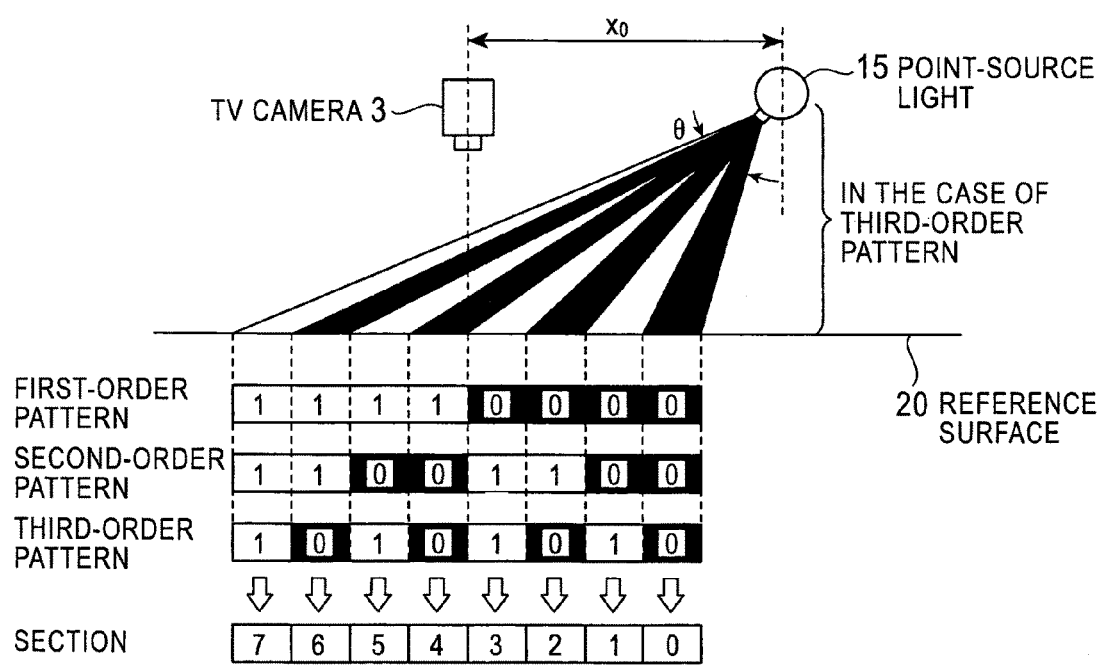
FIG. 15 is a diagram for describing a principle of binary-coded pattern projection method.

In FIG. 1 to FIG. 3, the description has been given for an example case where the display surface of the pattern displaying means is arranged orthogonal to the y-axis. However, the display surface does not have to be orthogonal to the y-axis. When a display screen of the flat-panel display 4 is arranged orthogonal to a virtual optical axis of a case where an optical axis of the TV camera 3 is reflected by the surface of the measurement target 1, such as, for example, a case shown in FIG. 14 as an embodiment (a third one) of the present invention, or when the display screen is appropriately arranged in a manner other than these cases, surface-distortion calculation equations (geometric relationship between the pattern displaying means, the capturing means, and the reference surface on which the measurement target is placed) similar to Equations (1) to (6) can be derived on the basis of a geometric relationship corresponding to each arrangement. The surface distortion can be calculated using these equations.

Any patterns can be employed as light-and-shade patterns displayed on the pattern displaying means as long as the patterns are coded so that coordinates (X, Z) of a position of an original image on the screen (or on the screen of the flat-panel display), coordinates (x, y, z) on the measurement-target surface, and coordinates (x', y') of a position of a mirror image captured by the TV camera can be associated with each other based on the geometric relationship in order to enable surface-distortion distribution calculation to be performed using the above-described simplified Equations (5) and (6).

Figure 4:
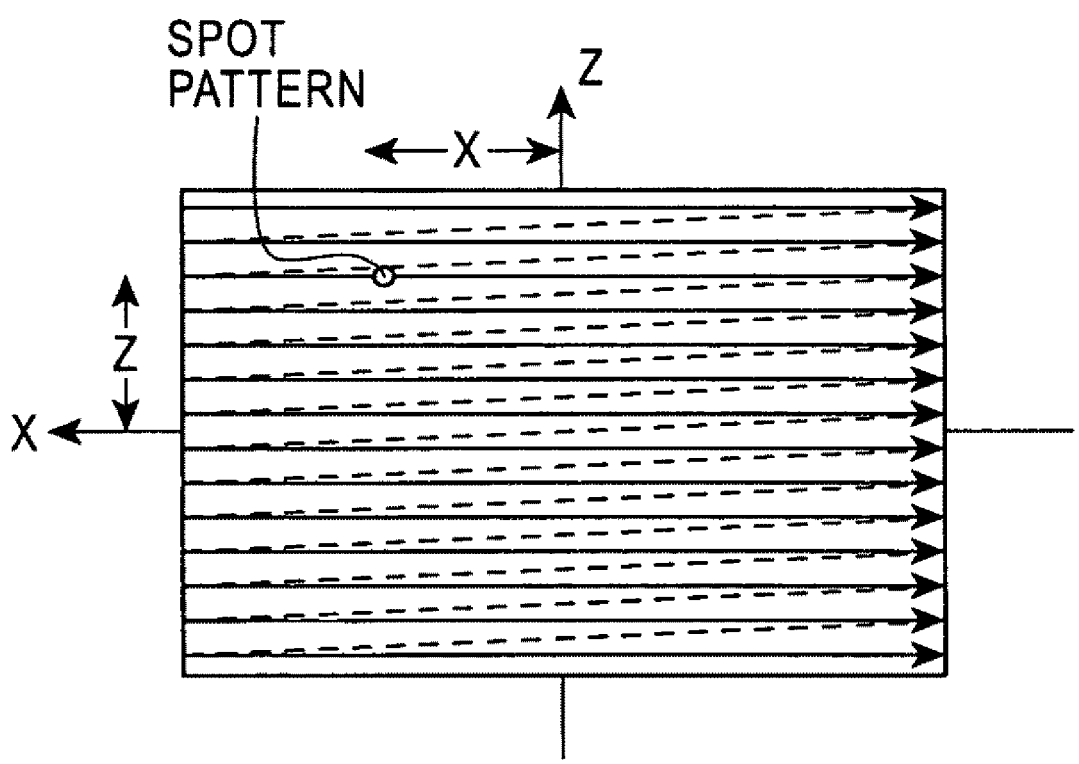
FIG. 4 is a diagram for describing spot pattern raster scanning that is one kind of light-and-shade pattern.

For example, light-and-shade pattern formed by raster scanning of a spot pattern as shown in FIG. 4 can be employed. The coordinates of the position of the mirror image correspond to an address of a pixel on the screen displaying the mirror image. Thus, in this case, the coordinates (X, Z) of the position of the original image can be associated with the coordinates (x', y') of the position of the mirror image by employing the display position of the spot pattern at the time that brightness of a pixel located at a pixel address becomes maximum during scanning of the spot pattern as data belonging to the pixel located at the pixel address.

In addition, for example, light-and-shade patterns formed by combination of vertical scanning of a slit 7 (horizontal slit) extending in the horizontal direction (the X-direction) as shown in FIG. 5A and horizontal scanning of a slit 7 (vertical slit) extending in the vertical direction (the Z-direction) as shown in FIG. 5B can be employed. In this case, the coordinate Z of the position of the original image can be associated with the coordinate y' of the position of the mirror image by employing the coordinate Z of the position of the original image of the horizontal slit at the time that the brightness of a pixel located at a pixel address becomes maximum during the vertical scanning of the horizontal slit as a data belonging to the pixel located at the pixel address. On the other hand, the coordinate X of the position of the original image can be associated with the coordinate x' of the position of the mirror image by employing the coordinate X of the position of the original image of the vertical slit at the time that the brightness of a pixel located at a pixel address becomes maximum during the horizontal scanning of the vertical slit as data belonging to the pixel located at the pixel address.

It takes a time to scan the whole display area of the pattern displaying means with the light-and-shade patterns of FIG. 4, FIG. 5A and FIG. 5B.

Accordingly, the scan time can be shortened by using multi-slit in which a plurality of slits are arranged in parallel to each other and at even intervals. However, there is a problem that it is difficult to distinguish the plurality of slits from one another in the multi-slit. In particular, when the degree of the surface distortion is significant, the mirror image is greatly distorted. Thus, it often becomes unknown that which slit on the mirror image corresponds to which slit on the original image with the multi-slit. In such a case, the reliability of association of the coordinates (X, Z) of the position of the original image and the coordinates (x', y') of the position of the mirror image is guaranteed only within a range divided by the slits.

To cope with such a case, the above-described plurality of kinds of stripe array patterns used for the binary-coded pattern projection method can be employed as light-and-shade patterns in the present invention. The plurality of kinds of stripe array patterns used for the binary-coded pattern projection method, which are binary-coded so that the interval, among intervals having the minimum stripe width in a direction orthogonal to the stripe-extending direction in the display area, of the position can be known by combination of the plurality of kinds of the stripe array patterns sequentially switched and displayed on the whole display area and the display order, are employed. The binary codes correspond to an order of appearance of "light" (1) and "shade" (0) at a pixel located at each pixel address during the sequential switching of the plurality of different stripe array patterns. Thus, the order of appearance of "light" (1) and "shade" (0) at the pixel located at each pixel address is stored during the sequential switching, and this stored result is binary-coded. Image processing for setting this binary-coded result as data of the pixel is executed for both cases where the direction orthogonal to the stripe-extending direction is set as the X-direction and the Z-direction. In such a manner, coarse association of the coordinates (X, Z) of the position of the original image and the coordinates (x', y') of the position of the mirror image is possible.

In the binary-coded pattern projection method, the minimum stripe width of the plurality of kinds of stripe array patterns corresponds to the minimum unit of the coordinates (X, Z) of the position of the original image and the minimum stripe width can not be made significantly small since it is difficult to determine whether a stripe boarder belongs a light portion or a shade portion. Accordingly, the projection method has a disadvantage that the resolution is low. For this reason, the association is described as the coarse association here.

Herein, the stripe width indicates the width of one area of a pair of light and shade of the stripe. The minimum stripe width means a narrower one of the widths of one of the light and shade areas.

On the other hand, light-and-shade patterns formed by combining a plurality of stripe array patterns used for the binary-coded pattern projection method with the multi-slit scanning have been known (see Patent Document 10). According to this, by simultaneously scanning each section having the minimum stripe width in the plurality of kinds of stripe array patterns with one slit of the multi-slit pattern, the fine position within each section can be recognized in a small amount of time, and finer association of coordinates (X, Z) of the position of the original image and coordinates (x', y') of the position of the mirror image can be performed.

Accordingly, in the present invention, it is preferable to employ a plurality of kinds of stripe array patterns used for the binary-coded pattern projection method and a plurality of slits, each scanning a range equal to or greater than the minimum stripe width as a plurality of kinds of light-and-shade patterns (corresponding to a fourth invention of the present invention).

In this case, from the standpoint of simplicity of image processing, regarding the plurality of kinds of stripe array patterns, the whole stripe array pattern is preferably equally divided into $2^n$ pieces, and light and shade are alternately arranged (corresponding to a fifth invention of the present invention). In addition, the plurality of slits (multi-slit) are preferably scanned in a direction orthogonal to the slit-extending direction (corresponding to a sixth invention of the present invention).

Figure 6:
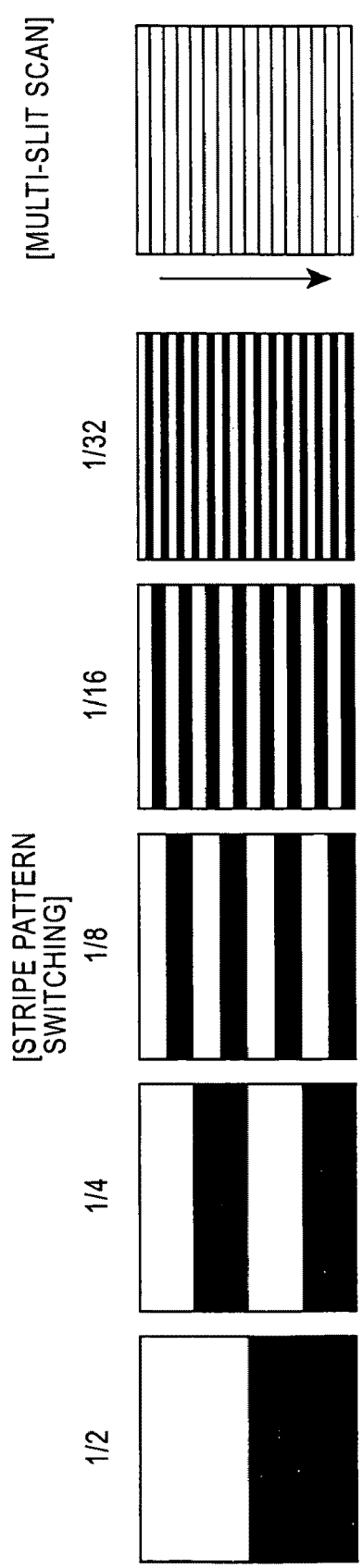
FIG. 6 is a diagram showing switching of stripe array patterns that extend in the horizontal direction and multi-slit scanning among light-and-shade patterns employed by the present invention.

As an example of such light-and-shade patterns, 5 kinds of stripe array patterns and one kind of multi-slit that extend in the horizontal direction (X-direction) are shown in FIG. 6. The stripe array patterns are those in which the whole stripe array pattern is divided into $2^n$ pieces and light and shade are alternately arranged. In this example, n=1 to 5. More specifically, n=1, 2, 3, 4, and 5 correspond to 5 kinds of patterns denoted by ½, ¼, ⅛, 1/16, and 1/32 on the left side of FIG. 6, respectively. Since these 5 kinds of stripe array patterns are sequentially switched and displayed, it is possible to perform coarse association (association between binary-coded sections) of a y-coordinate on the mirror image (coordinate y' of the position of the mirror image) and Z-coordinate on the pattern displaying means (coordinate Z of the position of the original image).

On the other hand, regarding the multi-slit, a plurality of slits are arranged at intervals of the minimum stripe width (stripe width of the 1/32 stripe array pattern) as shown on the right of FIG. 6. Projection of stripe array patterns up to ⅟₃₂ is not fixed. If the degree of the surface distortion is significant, it may become unknown that which stripe on the mirror image corresponds to which stripe on the original image before projecting the ⅟₃₂ stripe array pattern. Thus, the minimum stripe width of the pattern may be appropriately adjusted by human determination or the like.

In this multi-slit, an interval of minimum stripe width is maintained in the direction orthogonal to the slit-extending direction. An area not smaller than the minimum stripe width, preferably, an area slightly greater than the minimum stripe width and not greater than 1.3 times of the minimum stripe width, is scanned with each slit of the multi-slit. The reason why scanning of an area slightly greater than the minimum stripe width is preferable is because boarders are surely scanned and measurement of the surface distortion at the boarders can be surely performed. In this example, since every single slit scans each section having the minimum stripe width, it is possible to perform fine association of the coordinate y' of the position of the mirror image and the coordinate Z of the position of the original image within an identical binary-coded section corresponding to each section having the minimum stripe width.

In addition, when the directions of measuring the surface distortion are set to two directions orthogonal to each other, it is preferable to use a plurality of kinds of second stripe array patterns and a plurality of second slits having slits whose extending direction is orthogonal to that of the plurality of kinds of stripe patterns and the plurality of slits in one direction that is performed later, instead of the plurality of kinds of stripe array patterns and the multi-slit used in the measurement in the other direction that is performed first (corresponding to a seventh invention of the present invention).

Figure 10:
FIG. 10 is a diagram showing switching of stripe array patterns that extend in the vertical direction and multi-slit scanning among light-and-shade patterns employed by the present invention.

As an example thereof, FIG. 10 shows stripe array patterns and multi-slit extending in the vertical direction instead of each stripe array pattern and the multi-slit shown in FIG. 6. According to this, description in which y' and Z of the description of FIG. 6 are replaced with x' and X, respectively, is applied. Thus, it is possible to perform coarse association between the coordinate x' of a position of a mirror image and the coordinate X of a position of the original image and fine association between the coordinate x' of a position of a mirror image and the coordinate X of a position of the original image within an identical binary-coded section corresponding to each section having the minimum stripe width.

When patterns of FIG. 10 are used instead of those of FIG. 6, the number of kinds of stripe array patterns and the number of slits are the same before and after the change. However, the configuration is not limited to this, and the number of kinds of stripe array patterns and the number of slits may differ before and after the change.

When a plurality of kinds of stripe array patterns used for the binary-coded pattern projection method and a plurality of slits for scanning a range equal to or greater than the minimum stripe width shown, for example, in FIG. 6 and FIG. 10 are employed as a plurality of light-and-shade patterns, a procedure of image processing or surface-distortion distribution calculation performed by the surface-distortion distribution measuring means is preferably set, for example, as follows.

(A1) For each pixel of the capturing means, an order of appearance of light and shade at the pixel is stored during switching and displaying of the plurality of kinds of stripe array patterns. A value of coordinates, on the pattern displaying means, corresponding to the stored result of the appearance order, is determined. A value of coordinates, on the measurement-target surface, corresponding to the pixel is determined on the basis of the determined coordinate value, an address of the pixel, and a geometric relationship between the pattern displaying means, the capturing means, and the measurement target. Coarse surface-distortion distribution of the whole measurement-target surface (between binary-coded sections) is determined on the basis of the coordinate value on the pattern display means corresponding to the pixel and the coordinate value on the measurement-target surface corresponding to the pixel (corresponding to a tenth invention of the present invention).

(A2) The surface-distortion measuring device calculates surface-distortion distribution on the basis of the plurality of mirror images obtained by scanning the plurality of slits. For each pixel, a value of coordinates of a position of the slit-scanning on the pattern displaying means at the time that the corresponding pixel of the capturing means shows the maximum brightness during the scanning of the slits is determined as a value of coordinates on the pattern displaying means corresponding to the pixel. Fine surface-distortion distribution within a range equal to or greater than the minimum stripe width (within a binary coded section, here, sections are preferably distinguished on the basis of the result obtained by the series of processing steps of the above-described (A1) after the switching and displaying of the plurality of kinds of stripe array patterns) is determined on the basis of the determined coordinate value, an address of the corresponding pixel, and a geometric relationship between the pattern displaying means, the capturing means, and the measurement target. An image of the fine surface-distortion distribution is displayed (corresponding to an eleventh invention of the present invention).

(A3) The calculation result of the coarse surface-distortion distribution of the whole measurement-target surface determined in (A1) is complemented by the fine surface-distortion distribution determined in (A2) to determine the fine surface-distortion distribution of the whole measurement-target surface (corresponding to a twelfth invention of the present invention). Determining the coordinate value of the slit-scanning position on the pattern displaying means at the time that the pixel shows the maximum brightness as the coordinate value on the pattern displaying means corresponding to the pixel is related to, for example, a thirteenth invention of the present invention described next. Suppose that the number of pixels in the horizontal direction of the pattern displaying means is 1024 and the pixel that shows the maximum brightness on a pixel of the capturing means is the 512th pixel of the pattern displaying means. In such a case, this may be shown in gray that is an intermediate in the grayscale to display the state of the surface distortion as a black-and-white image. It is favorable to determine relative magnitude in the whole surface-distortion measurement-target surface at each position utilizing a fact that the scanning position that shows the maximum brightness differs depending on the position of pixel. Such an advantage is provided.

In addition, when only ultimate fine surface-distortion distribution of the whole measurement-target surface is desired to be determined, the surface-distortion distribution calculating steps of (A1) and (A2) can be omitted. A procedure of image processing or surface-distortion distribution calculation may be set, for example, as follows.

(B) The image processing or the surface-distortion distribution calculation performed by the surface-distortion distribution calculating means includes a step of storing, for each pixel of the capturing means, an order of appearance of light and shade at the pixel during switching and displaying of the plurality of kinds of stripe array patterns and of determining a value of coordinates, on the pattern displaying means, corresponding to the stored result of the appearance order as a value of coordinates on the pattern display means corresponding to the pixel, a step of determining, for each pixel, a value of coordinates of a position of the slit-scanning on the pattern displaying means at the time that the corresponding pixel of the capturing means shows the maximum brightness during the scanning of the slits as a value of coordinates on the pattern displaying means corresponding to the pixel, a step of combining the coordinate values to determine a value of coordinates on the pattern displaying means corresponding to each pixel, a step of determining, for all of pixels, surface-distortion distribution on the basis of the determined coordinate value, an address of each pixel, and a geometric relationship between the pattern displaying means, the capturing means, and the measurement target, and a step of displaying an image of an execution result obtained at one or more steps among the above-described steps (corresponding to a thirteenth invention of the present invention).

When a measuring device in which the procedure of the image processing or the surface-distortion distribution calculation performed by the surface-distortion distribution measuring means is set to the above-described (A1) to (A3) is employed, the following series of processing operations (AS1 to AS6) are performed as a method for measuring the surface distortion (corresponding to a fifteenth invention of the present invention).

(AS1) Processing for displaying a plurality of kinds of stripe array patterns used for a binary-coded pattern projection method on pattern displaying means capable of displaying given patterns.

(AS2) Processing for scanning and displaying a plurality of slits in a direction orthogonal to a direction in which the slits extend.

(AS3) Processing for capturing mirror images, reflected in the specular or semi-specular measurement-target surface, of the plurality of displayed stripe array patterns with capturing means.

(AS4) Processing for storing, for each pixel of the capturing means for capturing the mirror images, of the plurality of stripe array patterns used for the binary-coded pattern projection method, reflected in the measurement target, an order of appearance of light and shade at the pixel, for determining a value of coordinates, on the pattern displaying means, corresponding to the stored result of the order of appearance as a value of coordinates on the pattern displaying means corresponding to the pixel, for determining a value of coordinates on the measurement-target surface corresponding to the pixel on the basis of the determined coordinate value, an address of the pixel, and a geometric relationship between the pattern displaying means, the capturing means, and the measurement target, and for determining coarse surface-distortion distribution of the whole measurement-target surface on the basis of the coordinate value on the pattern display means corresponding to the pixel and the coordinate value on the measurement-target surface corresponding to the pixel (AS5) Processing for determining, for each pixel, a value of coordinates of a position of the slit-scanning on the pattern displaying means at the time that the pixel shows the maximum brightness during the scanning of the slits as a value of coordinates on the pattern displaying means corresponding to the pixel and displaying an image of the data, and for determining, for all of the pixels, fine surface-distortion distribution within a range equal to or greater than the minimum stripe width on the basis of the determined coordinate value, an address of the pixel, and a geometric relationship between the pattern displaying means, the capturing means, and the measurement target.

(AS6) Processing for determining fine surface-distortion distribution of the whole measurement-target surface by complementing the calculation result of the overall coarse surface-distortion distribution with the calculation result of the fine surface-distortion distribution.

In addition, when a measuring device in which the procedure of the image processing or the surface-distortion distribution calculation performed by the surface-distortion distribution measuring means is set to the above-described (B) is employed, the following processing operations may be performed as a method for measuring the surface distortion (corresponding to a sixteenth invention of the present invention).

(BS1) Processing for displaying a plurality of kinds of stripe array patterns used for a binary-coded pattern projection method on pattern displaying means capable of displaying given patterns.

(BS2) Processing for scanning and displaying a plurality of slits in a direction orthogonal to a direction in which the slits extend.

(BS3) Processing for capturing mirror images, reflected in the specular or semi-specular measurement-target surface, of the plurality of displayed stripe array patterns with capturing means.

(BS4) Processing for storing, for each pixel of the capturing means for capturing the mirror images, of the plurality of kinds of stripe array patterns used for the binary-coded pattern projection method, reflected in the measurement target, an order of appearance of light and shade at the pixel, for determining a value of coordinates, on the pattern displaying means, corresponding to the stored result of the order of appearance as a value of coordinates on the pattern displaying means corresponding to the pixel.

(BS5) Processing for determining, for each pixel, a value of coordinates of a position of the slit-scanning at the time that the pixel shows the maximum brightness during the scanning of the slits as a value of coordinates on the pattern displaying means corresponding to the pixel.

(BS6) Processing for combining the coordinate values determined in (BS4) and (BS5) to determine a value of coordinates on the pattern displaying means corresponding to each pixel and processing for determining, for all of pixels, surface-distortion distribution of the whole measurement-target surface on the basis of the determined coordinate value, an address of the pixel, and a geometric relationship between the pattern displaying means, the capturing means, and the measurement target.

(BS7) Processing for displaying an image of an execution result of an intermediate stage or a final stage of each processing.

Additionally, the rate of change in inclination of the surface is calculated by determining a second derivative of the inclination of the measurement-target surface and a position of the surface distortion and the degree of the surface distortion are evaluated quantitatively (corresponding to a fourteenth or seventeenth invention of the present invention).

Figure 16:
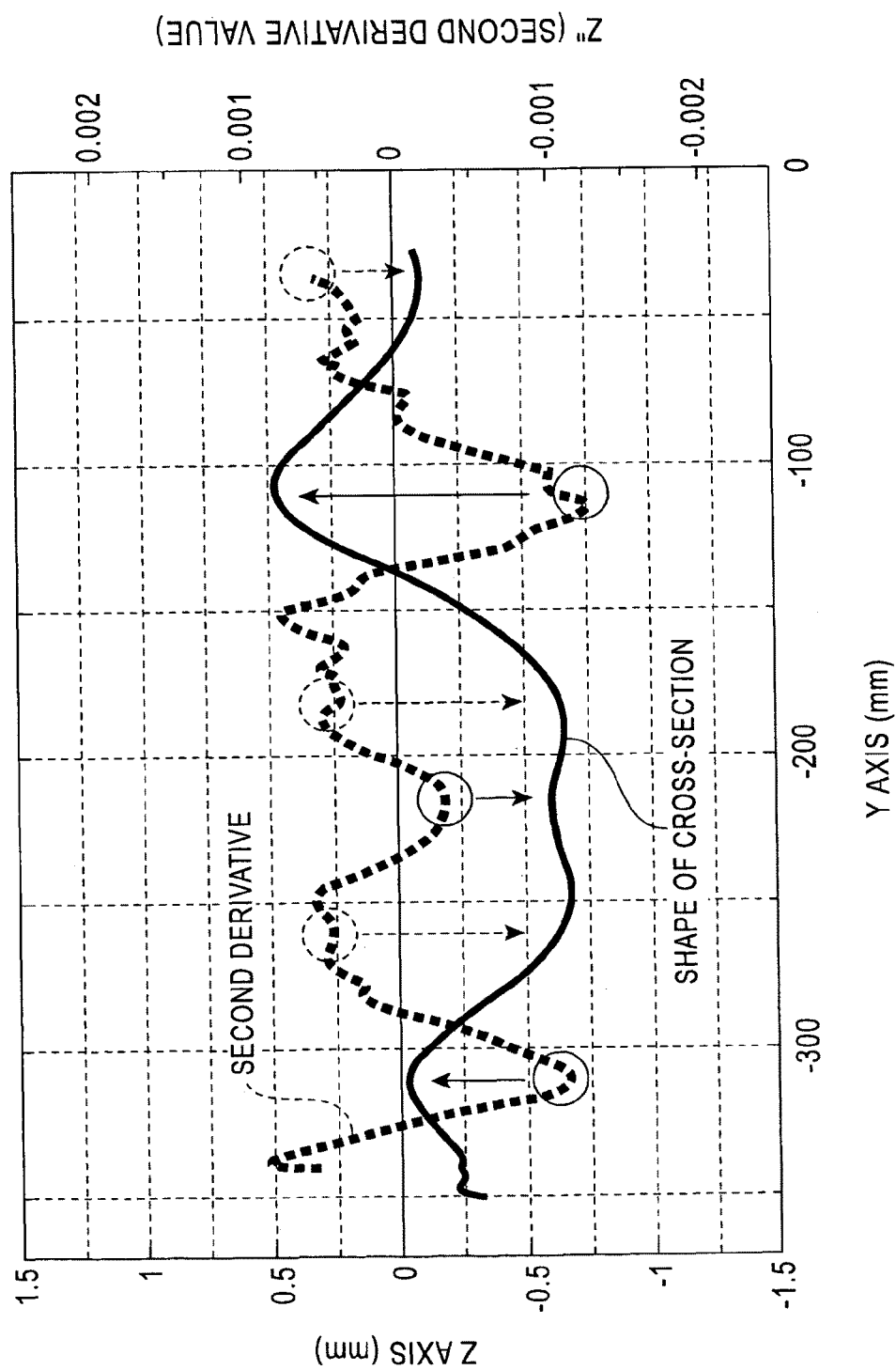
FIG. 16 is a diagram showing an example in which a cross-sectional shape and second derivative values are associated.

More specifically, the first derivative value of the cross-sectional shape, namely, the inclination of the surface, is determined using Equations (5) and (6), and curve fitting is performed on the values. Furthermore, approximation curve is differentiated to calculate the rate of change in the inclination (second derivative value). Calculation of the second derivative value is repeated for every cross-section to obtain distribution of second derivative values of the whole surface. FIG. 16 is a diagram showing an example in which cross-sectional shapes are associated with second derivative values. It is known that the cross-sectional shape is a convex curved surface at portions where the second derivative value is the relative minimum that is a negative value (positions enclosed by a solid circular line in the drawing). Conversely, it is known that the cross-sectional shape is a concave curved surface at portions where the second derivative value is the relative minimum that is a positive value (positions enclosed by a broken circular line in the drawing). Accordingly, by determining the second derivative values, it is possible to quantitatively evaluate the ruggedness of the surface, namely, a position of a surface distortion and the degree of the surface distortion. It is possible to perform digital differentiation using digital values. However, to reduce digital noises caused at that time, the approximation curve is used.

In addition, in a method for press-forming a metal plate, surface-distortion distribution of the press-formed metal plate is measured using the measuring device and/or the measuring method according to the above-described present invention. According to such a metal plate press-forming method, advantages of the present invention are shown in the clearest form. Thus, this press-forming method is also included in the scope of the present invention (corresponding to an eighteenth invention of the present invention).

Additionally, according to a surface quality inspecting method for inspecting a surface quality defect resulting from a surface distortion caused in at least one of metal plate processing steps of press-forming, component mounting, assembling, coating, heat treatment, and inspection of a finished product using the measuring device and/or the measuring method according to the above-described present invention, it is possible to cope with the speed of the manufacturing line that conveys the products, which cannot be coped with the conventional art. Since it is possible to perform inline inspection and to tremendously improve inspection accuracy and inspection efficiency, the surface quality inspecting method is also included in the scope of the present invention (corresponding to a nineteenth invention of the present invention).

According to each of the above-described inventions, restrictions resulting from limitation on resolution of an angle φ as in the case of Patent Document 10 are dissolved. Depending on fineness of the pixels of the pattern displaying means and the capturing means, it is possible perform quantitative measurement and evaluation of surface-distortion distribution equivalent to small ruggedness of approximately several tens micrometers on a specular surface or semi-specular surface, such as, for example, a surface of a vehicle outer panel.

An example of the present invention will be disclosed below as an example 1. In the example 1, the measuring device shown in FIG. 2 was employed. A sample obtained by press-forming and coating a vehicle outer panel was used as a measurement target. Surface-Distortion distribution was measured using the measuring method of the 16th invention of the present invention. Measurement directions were set to two directions, i.e., the y-direction and the x-direction (see FIG. 1). Light-and-shade patterns shown in FIG. 6 and FIG. 10 were used in measurement in the y-direction and measurement in the x-direction, respectively. The measuring device was arranged to satisfy l=L in FIG. 1. Equation (5) and Equation (6) were employed in the measurements in the x-direction and in the y-direction, respectively, as surface-distortion calculation equations. A DLP projector having 1024×768 pixels and a CCD TV camera having 600×480 pixels were employed as the projector and the TV camera, respectively.

Figure 7:
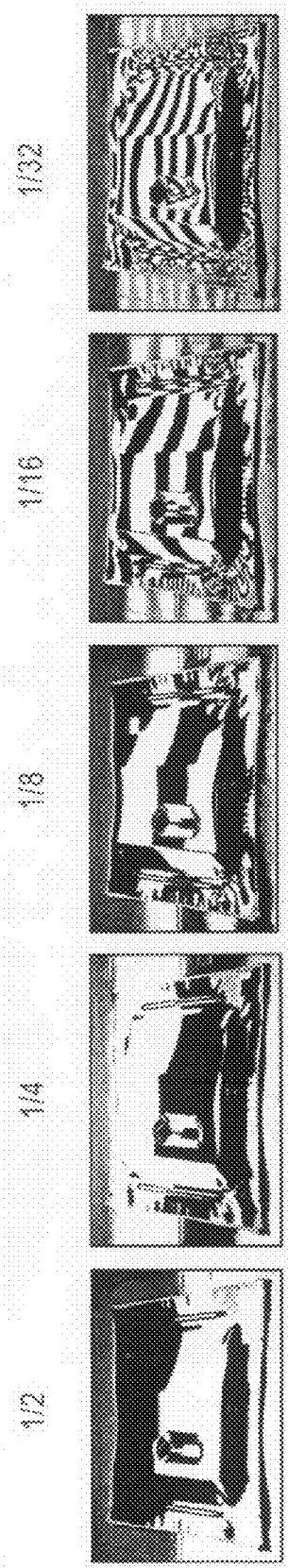
FIG. 7 is a diagram showing captured images of mirror images of light-and-shade patterns reflected in a measurement-target surface at each stage of coded pattern projection corresponding to switching of stripe array patterns using light-and-shade patterns of FIG. 6 and at each stage of multi-slit scanning.
Figure 7:
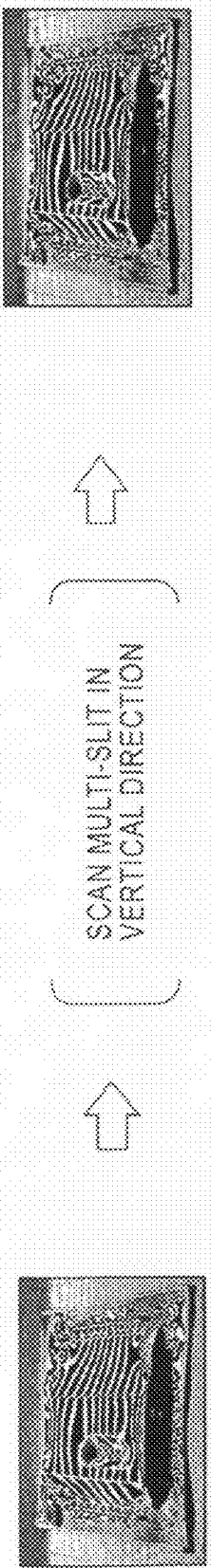

Firstly, measurement in the y-direction was performed. Switching of the stripe patterns of FIG. 6 (projection of coded patterns) was performed first, and then multi-slit scanning was performed. Mirror images of the light-and-shade patterns displayed on the screen reflected in the measurement-target surface were captured with the TV camera (The above-described processing of (BS1), (BS2), and (BS3)). The captured mirror images are shown in FIG. 7.

Figure 8A:
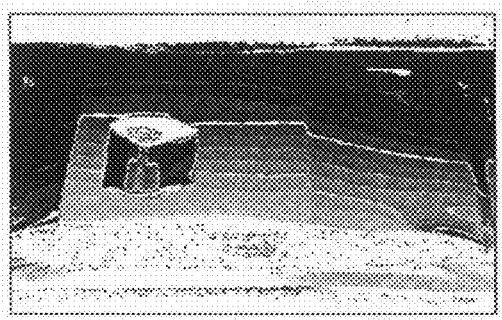
FIG. 8A is a diagram showing a displayed image representing pixel data (corresponding to coarse coordinates of a position in the Z-direction) obtained by performing image processing on a captured image at each stage of the coded pattern projection of FIG. 7 using light and shade.
Figure 8B:
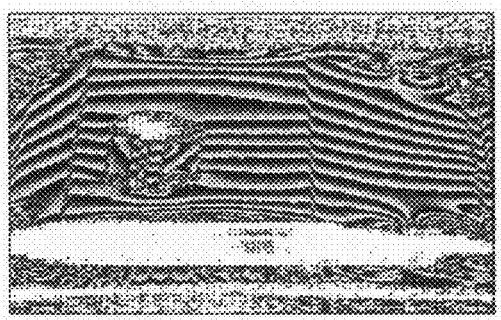
FIG. 8B is a diagram showing a displayed image representing pixel data (corresponding to fine coordinates of a position in a section of the coarse coordinates of the position in the Z-direction) obtained by performing image processing on a captured image at each stage of the multi-slit scanning of FIG. 7 using light and shade.

Processing of (BS4) and (BS7) was performed at the time of coded pattern projection and capturing of mirror images thereof, and processing of (BS5) and (BS7) was performed at the time of multi-slit scanning and capturing of mirror images thereof. A display image representing, for all pixels, values of coordinates (corresponding to the coarse coordinates of a position in the Z-direction) on the pattern displaying means corresponding to each pixel determined in the processing of (BS4) using light and shade is shown in FIG. 8A. A display image representing, for all pixels, values of coordinates (corresponding to fine coordinates of a position in a section of the coarse position coordinate in the Z-direction) on the pattern displaying means corresponding to each pixel determined in the processing of (BS5) using light and shade is shown in FIG. 8B.

Figure 8C:
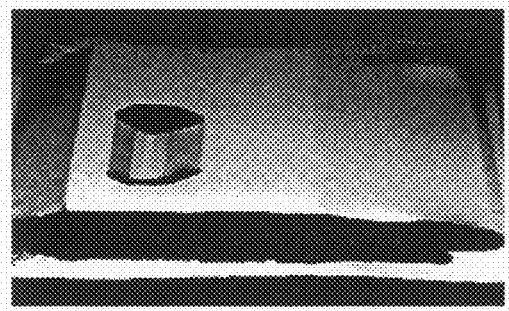
FIG. 8C is a diagram showing a displayed image representing pixel data (corresponding to a fine position in the Z-direction) obtained by combining pixel data of FIG. 8A and FIG. 8B using light and shade.
Figure 9:
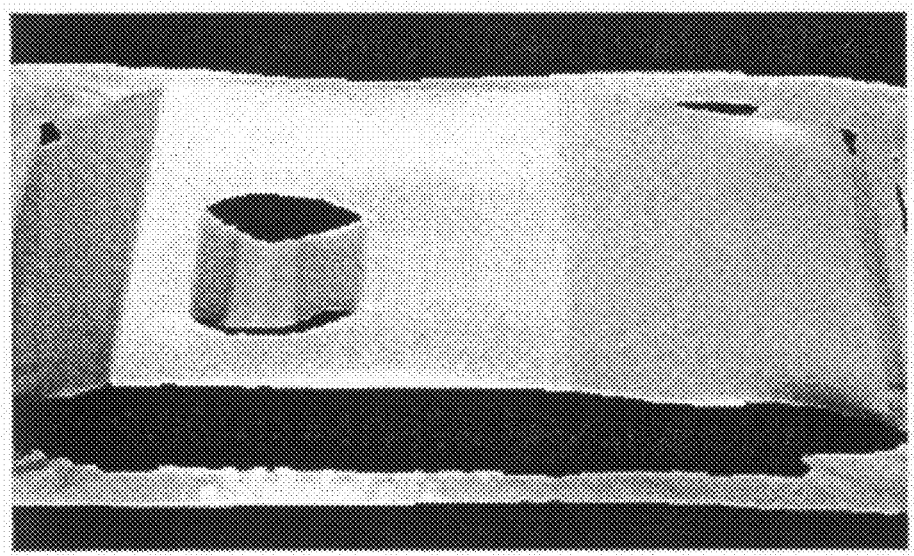
FIG. 9 is a diagram showing a displayed image representing a result of calculating surface-distortion distribution in the y-direction based on FIG. 8C.

Furthermore, processing of (BS6) and (BS7) was performed. An display image representing, for all pixels, values (corresponding to fine coordinates of positions in the Z-direction), obtained by combining the values of coordinates on the pattern displaying means corresponding to each pixel determined in the processing of (BS4) and the values of coordinates on the pattern displaying means corresponding to each pixel determined in the processing of (BS5), using light and shade is shown in FIG. 8C. At the time of this combination, noise treatment (noise-eliminating processing) was performed. A case of performing such noise treatment is also included in the present invention. Equation (6) was applied to a pair of y and Z values finely associated in such a manner to calculate surface-distortion (cos φ tan ε) distribution in the y-direction all over the measurement-target surface. A display image representing the result using light and shade is shown in FIG. 9.

Figure 11:
FIG. 11 is a diagram showing captured images of mirror images of light-and-shade patterns reflected in a measurement-target surface at each stage of coded pattern projection corresponding to switching of stripe array patterns using light-and-shade patterns of FIG. 10 and at each stage of multi-slit scanning.
Figure 11:
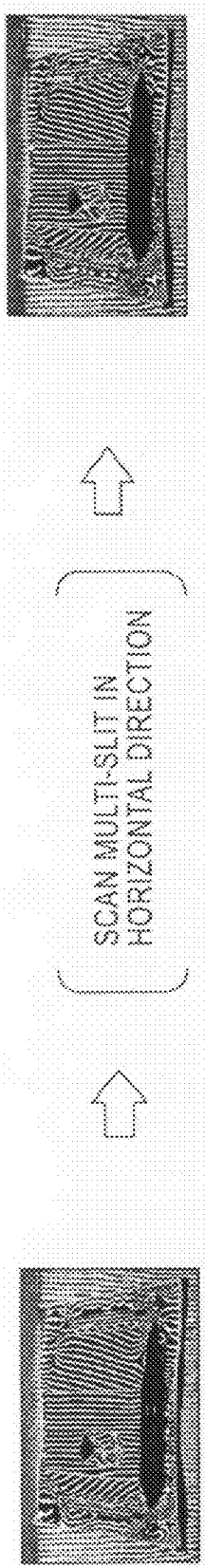

Measurement in the x-direction was performed next. Switching of the stripe patterns of FIG. 10 (projection of coded patterns) was performed first, and then multi-slit scanning was performed. Mirror images of the light-and-shade patterns displayed on the screen reflected in the measurement-target surface were captured with the TV camera (the above-described processing of (BS1), (BS2), and (BS3)). The captured mirror images are shown in FIG. 11.

Figure 12:
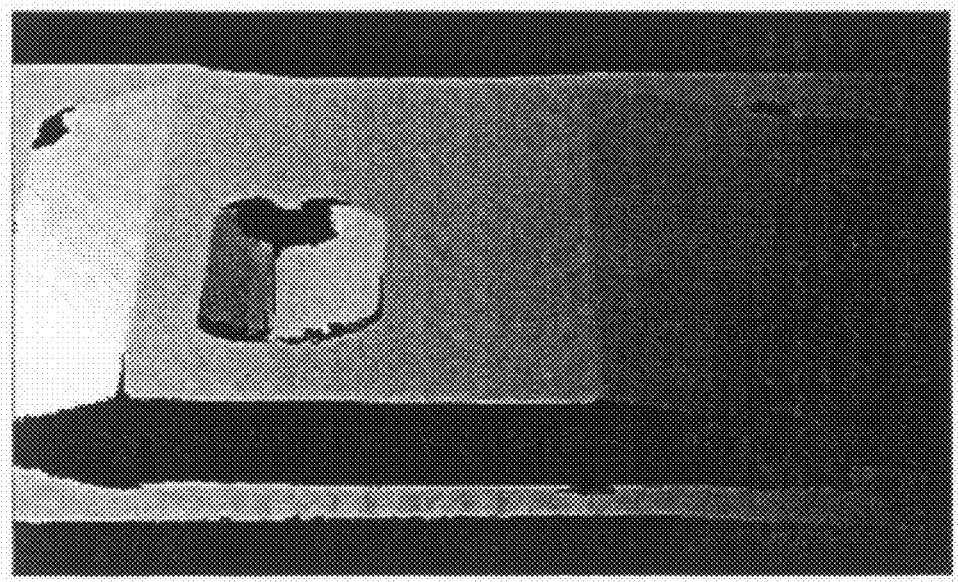
FIG. 12 is a diagram showing a displayed image representing pixel data (corresponding to a fine position in the X-direction) obtained by combining pixel data (corresponding to a coarse position in the X-direction) obtained by performing image processing on a captured image at each stage of coded pattern projection of FIG. 11 and pixel data (corresponding to a fine position in a section of the coarse position in the X-direction) obtained by performing image processing on an captured image at each stage of multi-slit scanning of FIG. 11 using light and shade.

Processing of (BS4) was performed at the time of coded pattern projection and capturing of mirror images thereof, and processing of (BS5) was performed at the time of multi-slit scanning and capturing of mirror images thereof. Furthermore, processing of (BS6) and (BS7) was performed. An display image representing, for all pixels, values (corresponding to fine coordinates of positions in the X-direction), obtained by combining the values of coordinates on the pattern displaying means corresponding to each pixel determined in the processing of (BS4) and the values of coordinates on the pattern displaying means corresponding to each pixel determined in the processing of (BS5), using light and shade is shown in FIG. 12.

Figure 13:
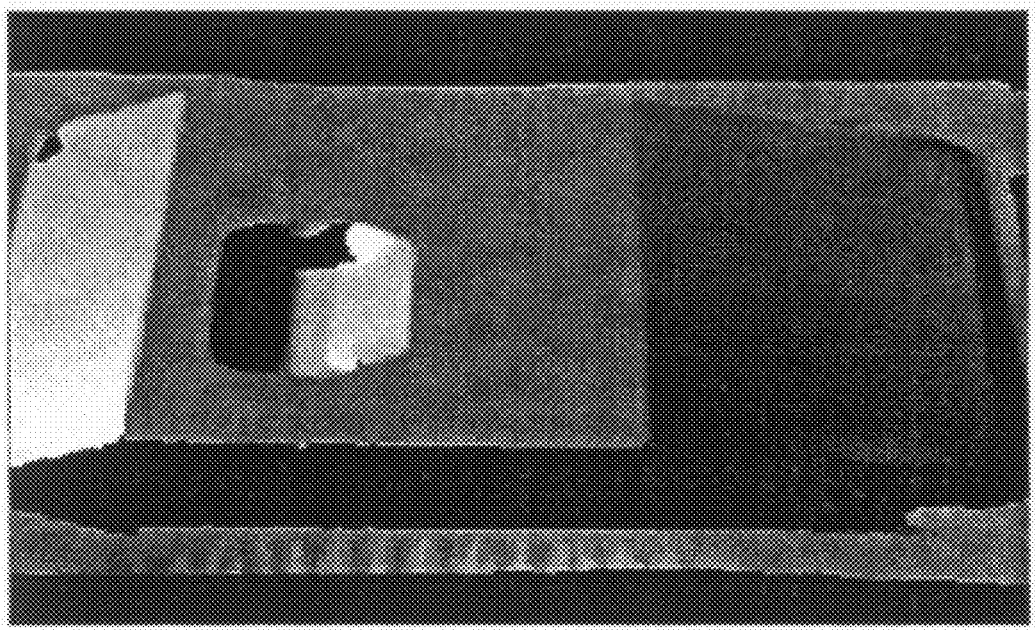
FIG. 13 is a diagram showing a displayed image representing a result of calculating surface-distortion distribution in the x-direction from pixel data of FIG. 12 using light and shade.

At the time of this combination, noise treatment (noise-eliminating processing) was performed. Equation (5) was applied to a pair of x and X values finely associated in such a manner to calculate surface-distortion (sin φ tan ε) distribution in the x-direction all over the measurement-target surface. A display image representing the result using light and shade is shown in FIG. 13.

As is clear from the example 1, according to the present invention, it is possible to quantitatively, rapidly, and highly accurately measure surface-distortion distribution at all of observable points on a specular or semi-specular surface of a target of measurement.

An example of the present invention will be disclosed next as an example 2. In the example 2, the measuring device shown in FIG. 2 was employed. A sample obtained by press-forming and coating a vehicle outer panel was used as a measurement target. The rate of change in inclination of the surface (=curvature) was calculated by determining a second derivative to quantitatively evaluate the position having the surface distortion and the degree of the distortion according to the measuring method of the fourteenth invention of the present invention.

Figure 17:
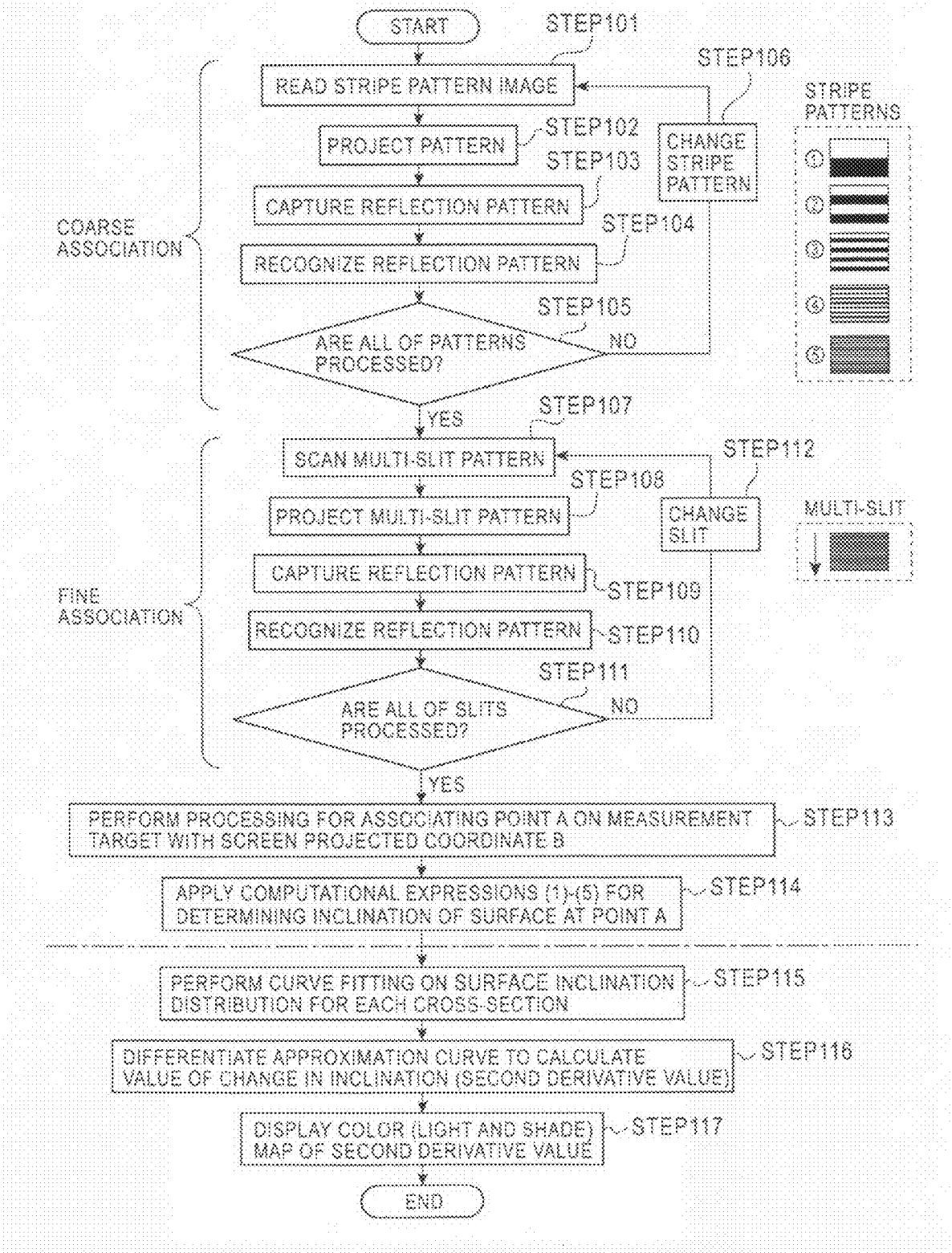
FIG. 17 is a diagram showing the entire processing flow in an example 2.

FIG. 17 is a diagram showing the entire processing flow in the example 2. Processing steps shown above a chain line are the same as those of the above-described example 1, and processing steps (STEP 115 to STEP 117) shown below the chain line are newly added.

The above-described coarse association and the above-described fine association are performed in the processing at STEP 101 to STEP 106 and in the processing at STEP 107 to STEP 112, respectively. At STEP 113 and STEP 114, the inclination of the surface, namely, the first derivative value (hereinafter, also referred to as a TRiDY value) of the cross-sectional shape, is determined.

Figure 18B:
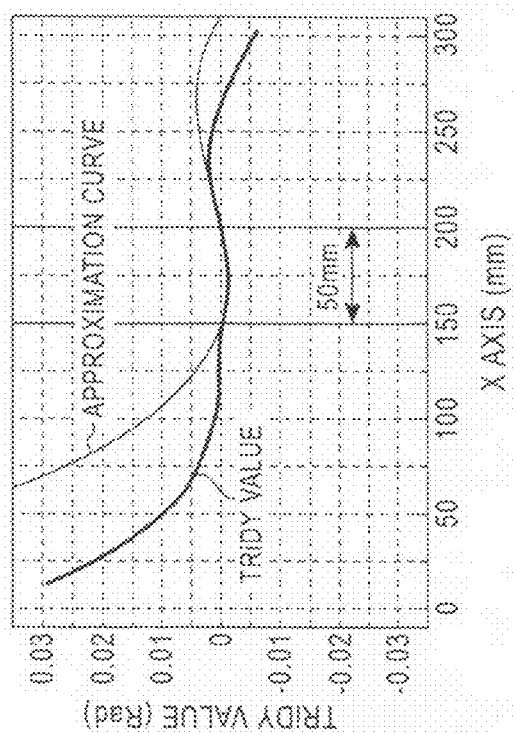
FIG. 18A and FIG. 18B are diagrams showing examples of an approximation curve of first derivative values of a cross-sectional shape.
Figure 18A:
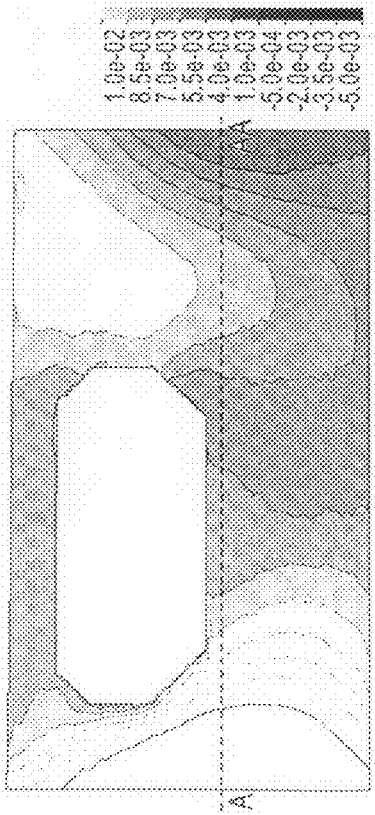

At STEP 115, curve fitting is performed on the distribution of surface inclination for each cross section. FIG. 18 is a diagram showing an example of an approximation curve of the first derivative value of the cross-sectional shapes. FIG. 18A and FIG. 18B are diagrams showing surface inclination distribution around a doorknob and the TRiDY value and the approximation curve at the cross section A-AA, respectively.

In this example, Equation (7) given below is determined as the approximation curve f'(x) of the TRiDY value using a least-squared method. It is known that the curves closely resemble as shown in FIG. 18B when the range of approximation is set to 50 mm, which is most suitable to the surface-distortion sensory evaluation result.

$$f'(x) = 1.13 \cdot 10^{-1} - 1.69 \cdot 10^{-3}x + 8.07 \cdot 10^{-6}x^2 - 1.22 \cdot 10^{-8}x^3 \quad (7)$$

Although an example of a polynomial using the least-squared method has been shown as an example of the approximation curve, the present invention is not limited to this.

At STEP 116, the approximation curve f'(x) of the TRiDY value determined using Equation (7) is further differentiated as shown in Equation (8) given below to determine the second derivative value (curvature) f''(x). This processing is repeated on all of the cross sections to determine distribution of second derivative values of the surface.

Figure 19:
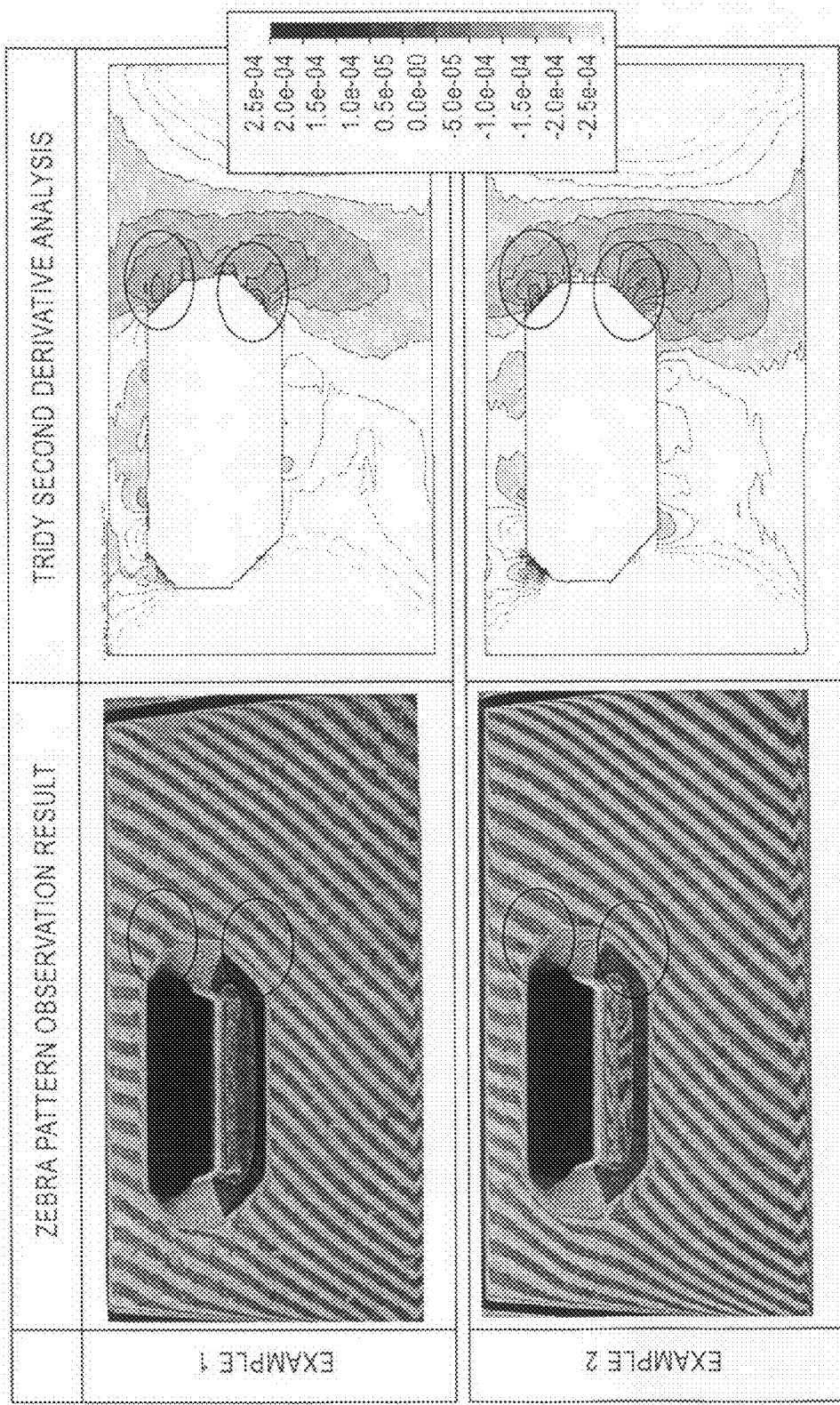
FIG. 19 is a diagram showing comparison of surface-distortion evaluation results according to an experiment and the present invention.

Finally, after displaying a color (or light-and-shade) map of the second derivative values (STEP 117), and the process is terminated. FIG. 19 is a diagram showing comparison of surface-distortion evaluation results according to an experiment and the present invention. The drawing shows, regarding two kinds of steel plate of different materials, zebra pattern display resulting from the experiment on the left and result obtained by applying the present invention on the right in a comparable manner, respectively.

$$f''(x) = -1.69 \cdot 10^{-3} + 2 \cdot 8.07 \cdot 10^{-6}x - 3 \cdot 1.22 \cdot 10^{-8}x^2 \quad (8)$$

The zebra pattern observation is for evaluating an appearance defect due to surface distortion by irradiating a light source having black-and-white linear stripes (zebra pattern display) to a coated-and-pressed product. When the irradiated parallel lines look distorted, it can be determined that the surface distortion is caused. Thus, distortions can be recognized at a boarder of the doorknob enclosed by a circle.

On the contrary, the present invention can quantitatively evaluate a position of a surface distortion and the degree of the distortion by a color (or light-and-shade) map of the second derivative values. Thus, if a surface distortion is caused at the same position where generation of the surface distortion is observed in the zebra pattern observation, the distortion can be confirmed on the light-and-shade map.

As is clear from the above-described example 2, according to the present invention, it is possible to quantitatively, rapidly, and highly accurately measure surface-distortion distribution at all of observable points on a specular or semi-specular surface of a target of measurement. In addition, it is possible to calculate the rate of change in inclination of a surface by performing differentiation on the inclination of the measurement-target surface twice and to quantitatively evaluate a position of a surface distortion and the degree of the distortion.

INDUSTRIAL APPLICABILITY

According to the present invention, it is possible to quantitatively, rapidly, and highly accurately measure surface-distortion distribution at all of observable points on a specular or semi-specular surface of a measurement target, and to accurately performing evaluation of the machinability of material metal plate, evaluation of the deterioration of press-forming die, and inspection of product metal plate in development of material metal plate used for presswork or the like. For example, the efficiency in development of highly effective material metal plates and processing method thereof is increased. The present invention contributes to improvement of the yield and quality of product metal plates.

The invention claimed is:

1. A device for measuring a surface distortion on a specular surface or a semi-specular surface, comprising:
    pattern displaying means capable of switching and displaying a plurality of kinds of light-and-shade patterns using a plurality of kinds of stripe array patterns used for a binary-coded pattern projection method and a plurality of slits, each of which scans a range equal to or greater than a minimum stripe width;
    capturing means for capturing mirror images, reflected in the specular or semi-specular measurement-target surface, of the plurality of light-and-shade patterns displayed on the pattern displaying means; and
    surface-distortion distribution calculating means for performing image processing on the captured mirror images of the plurality of light-and-shade patterns to calculate surface-distortion distribution of the measurement-target surface.

2. The device for measuring a surface distortion on a specular surface or a semi-specular surface according to claim 1, comprising: pattern displaying means capable of displaying the mirror images captured by the capturing means as images.

3. The device for measuring a surface distortion on a specular surface or a semi-specular surface according to claim 1, comprising: measurement-calculation-result displaying means capable of displaying at least one of a processing result of an intermediate stage or a final stage of the image processing and a surface-distortion calculation result.

4. The device for measuring a surface distortion on a specular surface or a semi-specular surface according to claim 1, wherein the plurality of kinds of stripe array patterns are patterns in which the whole area of a stripe array pattern is equally divided into $2^n$ pieces and light and shade are alternately arranged.

5. The device for measuring a surface distortion on a specular surface or a semi-specular surface according to claim 1, wherein the plurality of slits are scanned in a direction orthogonal to a direction in which the slits extend.

6. The device for measuring a surface distortion on a specular surface or a semi-specular surface according to claim 1, wherein a plurality of kinds of second stripe array patterns and a plurality of second slits, whose extending directions are orthogonal to those of the plurality of kinds of stripe array patterns and the plurality of slits, are used instead of the plurality of kinds of stripe array patterns and the plurality of slits.

7. The device for measuring a surface distortion on a specular surface or a semi-specular surface according to claim 1, wherein the pattern displaying means is constituted by a projector capable of projecting given patterns and a screen.

8. The device for measuring a surface distortion on a specular surface or a semi-specular surface according to claim 1, wherein the pattern displaying means is constituted by a flat-panel display capable of displaying given patterns.

9. The device for measuring a surface distortion on a specular surface or a semi-specular surface according to claim 1, the surface-distortion measuring device calculating the surface-distortion distribution on the basis of mirror images of the plurality of kinds of stripe array patterns used for the binary-coded pattern projection method, wherein the device stores, for each pixel of the capturing means, an order of appearance of light and shade at the pixel during switching and displaying of the plurality of kinds of stripe array patterns, determines a value of coordinates, on the pattern displaying means, corresponding to the stored result of the appearance order, determines a value of coordinates, on the measurement-target surface, corresponding to the pixel on the basis of the determined coordinate value, an address of the pixel, and a geometric relationship between the pattern displaying means, the capturing means, and the measurement target, and determines coarse surface-distortion distribution of the whole measurement-target surface on the basis of the coordinate value on the pattern display means corresponding to the pixel and the coordinate value on the measurement-target surface corresponding to the pixel.

10. The device for measuring a surface distortion on a specular surface or a semi-specular surface according to claim 9, the surface-distortion measuring device calculating surface-distortion distribution on the basis of the plurality of mirror images obtained by scanning the plurality of slits, wherein the device determines, for each pixel, a value of coordinates of a position of the slit-scanning on the pattern displaying means at the time that the corresponding pixel of the capturing means shows the maximum brightness during the scanning of the slits as a value of coordinates on the pattern displaying means corresponding to the pixel, determines fine surface-distortion distribution within a range equal to or greater than the minimum stripe width on the basis of the determined coordinate value, an address of the corresponding pixel, and a geometric relationship between the pattern displaying means, the capturing means, and the measurement target, and displays an image of the fine surface-distortion distribution.

11. The device for measuring a surface distortion on a specular surface or a semi-specular surface according to claim 10, wherein the calculation result of the coarse surface-distortion distribution of the whole measurement-target surface determined on the basis of the mirror images of the plurality of kinds of stripe array patterns used for the binary-coded pattern projection method is complemented by the fine surface-distortion distribution within the range equal to or greater than the minimum stripe width determined on the basis of the plurality of mirror images obtained by scanning the plurality of slits to determine fine surface-distortion distribution of the whole measurement-target surface.

12. The device for measuring a surface distortion on a specular surface or a semi-specular surface according to claim 1, wherein the image processing or the surface-distortion distribution calculation performed by the surface-distortion distribution calculating means includes a step of storing, for each pixel of the capturing means, an order of appearance of light and shade at the pixel during switching and displaying of the plurality of kinds of stripe array patterns and of determining a value of coordinates, on the pattern displaying means, corresponding to the stored result of the appearance order as a value of coordinates on the pattern display means corresponding to the pixel, a step of determining, for each pixel, a value of coordinates of a position of the slit-scanning on the pattern displaying means at the time that the corresponding pixel of the capturing means shows the maximum brightness during the scanning of the slits as a value of coordinates on the pattern displaying means corresponding to the pixel, a step of combining the coordinate values to determine a value of coordinates on the pattern displaying means corresponding to each pixel, a step of determining, for all of pixels, surface-distortion distribution on the basis of the determined coordinate value, an address of each pixel, and a geometric relationship between the pattern displaying means, the capturing means, and the measurement target, and a step of displaying an image of an execution result obtained at one or more steps among the above-described steps.

13. The device for measuring a surface distortion on a specular surface or a semi-specular surface according to claim 1, wherein the rate of change in inclination of the surface is calculated by determining a second derivative of the inclination of the measurement-target surface and a position of the surface distortion and the degree of the surface distortion are evaluated quantitatively.

14. A method for measuring a surface distortion on a specular surface or a semi-specular surface, wherein the method comprises performing:
displaying a plurality of kinds of stripe array patterns used for a binary-coded pattern projection method on pattern displaying means capable of displaying given patterns;
scanning and displaying a plurality of slits in a direction orthogonal to a direction in which the slits extend;
capturing mirror images, reflected in the specular or semi-specular measurement-target surface, of the plurality of displayed stripe array patterns with capturing means;
storing in the memory of a device, for each pixel of the capturing means for capturing the mirror images, of the plurality of stripe array patterns used for the binary-coded pattern projection method, reflected in the measurement target, an order of appearance of light and shade at the pixel, for determining a value of coordinates, on the pattern displaying means, corresponding to the stored result of the order of appearance as a value of coordinates on the pattern displaying means corresponding to the pixel, for determining a value of coordinates on the measurement-target surface corresponding to the pixel on the basis of the determined coordinate value, an address of the pixel, and a geometric relationship between the pattern displaying means, the capturing means, and the measurement target, and for determining coarse surface-distortion distribution of the whole measurement-target surface on the basis of the coordinate value on the pattern display means corresponding to the pixel and the coordinate value on the measurement-target surface corresponding to the pixel;

using a processing device to determine, for each pixel, a value of coordinates of a position of the slit-scanning on the pattern displaying means at the time that the pixel shows the maximum brightness during the scanning of the slits as a value of coordinates on the pattern displaying means corresponding to the pixel and displaying an image of the data, and for determining, for all of the pixels, fine surface-distortion distribution within a range equal to or greater than the minimum stripe width on the basis of the determined coordinate value, an address of the pixel, and a geometric relationship between the pattern displaying means, the capturing means, and the measurement target; and using a processing device to determine fine surface-distortion distribution of the whole measurement-target surface by complementing the calculation result of the overall coarse surface-distortion distribution with the calculation result of the fine surface-distortion distribution.

15. A method for measuring a surface distortion on a specular surface or a semi-specular surface, wherein the method comprises performing:

displaying a plurality of kinds of stripe array patterns used for a binary-coded pattern projection method on pattern displaying means capable of displaying given patterns;

scanning and displaying a plurality of slits in a direction orthogonal to a direction in which the slits extend;

capturing mirror images, reflected in the specular or semi-specular measurement-target surface, of the plurality of displayed stripe array patterns with capturing means;

storing in the memory of a device, for each pixel of the capturing means for capturing the mirror images, of the plurality of kinds of stripe array patterns used for the binary-coded pattern projection method, reflected in the measurement target, an order of appearance of light and shade at the pixel, for determining a value of coordinates, on the pattern displaying means, corresponding to the stored result of the order of appearance as a value of coordinates on the pattern displaying means corresponding to the pixel;

using a processing device to determine, for each pixel, a value of coordinates of a position of the slit-scanning at the time that the pixel shows the maximum brightness during the scanning of the slits as a value of coordinates on the pattern displaying means corresponding to the pixel;

using a processing device to combine the coordinate values to determine a value of coordinates on the pattern displaying means corresponding to each pixel;

using a processing device to determine, for all of pixels, surface-distortion distribution of the whole measurement-target surface on the basis of the determined coordinate value, an address of the pixel, and a geometric relationship between the pattern displaying means, the capturing means, and the measurement target; and displaying an image of an execution result of an intermediate stage or a final stage of each processing.

16. The method for measuring a surface distortion on a specular surface or a semi-specular surface according to claim 14, wherein the rate of change in inclination of the surface is calculated by determining a second derivative of the inclination of the measurement-target surface and a position of the surface distortion and the degree of the surface distortion are evaluated quantitatively.

17. A method for press-forming a metal plate, wherein surface-distortion distribution of the press-formed metal plate is measured using at least one of:

a device for measuring a surface distortion on a specular surface or a semi-specular surface comprising: pattern displaying means capable of switching and displaying a plurality of kinds of light-and-shade patterns; capturing means for capturing mirror images, reflected in the specular or semi-specular measurement-target surface, of the plurality of light-and-shade patterns displayed on the pattern displaying means; and surface-distortion distribution calculating means for performing image processing on the captured mirror images of the plurality of light-and-shade patterns to calculate surface-distortion distribution of the measurement-target surface; and the method for measuring a surface distortion on a specular surface or a semi-specular surface according to claim 14.

18. A method for inspecting quality of a surface of a metal product, wherein a surface quality defect resulting from a surface distortion caused in at least one of metal plate processing steps of press-forming, component mounting, assembling, coating, heat treatment, and inspection of a finished product is inspected using at least one of:

a device for measuring a surface distortion on a specular surface or a semi-specular surface comprising pattern displaying means capable of switching and displaying a plurality of kinds of light-and-shade patterns; capturing means for capturing mirror images, reflected in the specular or semi-specular measurement-target surface, of the plurality of light-and-shade patterns displayed on the pattern displaying means; and surface-distortion distribution calculating means for performing image processing on the captured mirror images of the plurality of light-and-shade patterns to calculate surface-distortion distribution of the measurement-target surface; and the method for measuring a surface distortion on a specular surface or a semi-specular surface according to claim 14.

* * * * *